United States Patent
Matthiesen et al.

(10) Patent No.: US 11,118,214 B2
(45) Date of Patent: *Sep. 14, 2021

(54) HYBRIDIZATION COMPOSITIONS AND METHODS

(75) Inventors: Steen Hauge Matthiesen, Hillerod (DK); Kenneth H. Petersen, Smorum (DK); Tim Svenstrup Poulsen, Horsholm (DK); Charles M. Hansen, Horsholm (DK)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 1055 days.

This patent is subject to a terminal disclaimer.

(21) Appl. No.: 12/994,492

(22) PCT Filed: May 27, 2009

(86) PCT No.: PCT/IB2009/005893
§ 371 (c)(1),
(2), (4) Date: May 20, 2011

(87) PCT Pub. No.: WO2009/144581
PCT Pub. Date: Dec. 3, 2009

(65) Prior Publication Data
US 2011/0229975 A1    Sep. 22, 2011

Related U.S. Application Data

(60) Provisional application No. 61/155,683, filed on Feb. 26, 2009, provisional application No. 61/056,089, filed on May 27, 2008.

(30) Foreign Application Priority Data

May 27, 2008 (DK) .............................. PA200800727
Feb. 27, 2009 (DK) .............................. PA200900278

(51) Int. Cl.
*G01N 33/50* (2006.01)
*C12Q 1/6832* (2018.01)
(Continued)

(52) U.S. Cl.
CPC ......... *C12Q 1/6832* (2013.01); *C12Q 1/6841* (2013.01); *Y10T 436/143333* (2015.01)

(58) Field of Classification Search
CPC ...... C12N 15/10; C12N 15/63; C07C 275/40; C07C 273/10; C12Q 1/6841; C12Q 1/6832; C12Q 2527/125
(Continued)

(56) References Cited

U.S. PATENT DOCUMENTS 4,652,517 A    3/1987   Scholl et al.
4,886,741 A    12/1989  Schwartz
(Continued)

FOREIGN PATENT DOCUMENTS

EA    005581 B1    4/2005
EP    0261955 A2   3/1988
(Continued)

OTHER PUBLICATIONS

Wahl et al.(1979). Efficient transfer of large DNA fragments from agarose gels to diazobenzyloxymethyl-paper and rapid hybridization by using dextran sulfate. Proc. Natl. Acad. Sci. USA. Biochemisty. vol. 76: 8: 3683-3687.*
(Continued)

*Primary Examiner* — Rebecca M Fritchman

(57) ABSTRACT

The invention provides methods and compositions for hybridizing at least one molecule to a target. The invention may, for example, eliminate the use of or reduce the dependence on formamide in hybridization. Compositions for use in the invention include an aqueous composition comprising at least one nucleic acid sequence and at least one polar (Continued)

aprotic solvent in an amount effective to denature double-stranded nucleotide sequences.

31 Claims, 2 Drawing Sheets

(51) Int. Cl.
  *C12Q 1/6841* (2018.01)
  *C07H 1/00* (2006.01)

(58) Field of Classification Search
  USPC .......................................... 435/455; 564/50
  See application file for complete search history.

(56) References Cited

U.S. PATENT DOCUMENTS

| | | | |
|---|---|---|---|
| 4,888,278 A | | 12/1989 | Singer et al. |
| 4,996,359 A | * | 2/1991 | Kesling et al. .................. 564/50 |
| 5,106,730 A | | 4/1992 | Van Ness et al. |
| 5,132,207 A | | 7/1992 | Kohne et al. |
| 5,382,285 A | | 1/1995 | Morrison |
| 5,432,065 A | | 7/1995 | Fuller |
| 5,521,061 A | | 5/1996 | Bresser et al. |
| 5,525,492 A | | 6/1996 | Hill |
| 5,527,675 A | | 6/1996 | Coull et al. |
| 5,539,082 A | | 7/1996 | Nielsen et al. |
| 5,582,985 A | | 12/1996 | Thompson |
| 5,623,049 A | | 4/1997 | Lobberding et al. |
| 5,633,129 A | | 5/1997 | Karger et al. |
| 5,650,148 A | | 7/1997 | Gage et al. |
| 5,705,333 A | | 1/1998 | Shah et al. |
| 5,714,331 A | | 2/1998 | Buchardt et al. |
| 5,718,915 A | | 2/1998 | Virtanen et al. |
| 5,736,336 A | | 4/1998 | Buchardt et al. |
| 5,750,340 A | * | 5/1998 | Kim ..................... C12Q 1/6841 |
| | | | 435/40.5 |
| 5,766,855 A | | 6/1998 | Buchardt et al. |
| 5,773,571 A | | 6/1998 | Nielsen et al. |
| 5,786,461 A | | 7/1998 | Buchardt et al. |
| 5,837,459 A | | 11/1998 | Berg et al. |
| 5,856,089 A | | 1/1999 | Wang et al. |
| 5,858,671 A | | 1/1999 | Jones |
| 5,869,237 A | | 2/1999 | Ward et al. |
| 5,891,625 A | | 4/1999 | Buchardt et al. |
| 5,919,894 A | | 7/1999 | Schubart |
| 5,925,744 A | | 7/1999 | Haner et al. |
| 5,962,227 A | | 10/1999 | Hedrick et al. |
| 5,972,610 A | | 10/1999 | Buchardt et al. |
| 5,986,053 A | | 11/1999 | Ecker et al. |
| 6,107,470 A | | 8/2000 | Nielsen et al. |
| 6,201,103 B1 | | 3/2001 | Nielsen et al. |
| 6,203,977 B1 | | 3/2001 | Ward et al. |
| 6,228,982 B1 | | 5/2001 | Norden et al. |
| 6,331,618 B1 | | 12/2001 | Bloch et al. |
| 6,344,315 B1 | | 2/2002 | Gray et al. |
| 6,357,163 B1 | | 3/2002 | Buchardt et al. |
| 6,361,940 B1 | | 3/2002 | Van Ness et al. |
| 6,475,720 B1 | * | 11/2002 | Gray ..................... C12Q 1/6827 |
| | | | 435/6.14 |
| 6,555,670 B1 | | 4/2003 | Aizawa et al. |
| 6,586,176 B1 | | 7/2003 | Trnovsky et al. |
| 6,656,685 B2 | | 12/2003 | Utermohlen et al. |
| 6,656,734 B1 | * | 12/2003 | Bischoff ................ C12N 15/87 |
| | | | 435/455 |
| 6,670,461 B1 | | 12/2003 | Wengel et al. |
| 6,794,499 B2 | | 9/2004 | Wengel et al. |
| 6,949,368 B2 | | 9/2005 | Chakrabarti et al. |
| 7,034,133 B2 | | 4/2006 | Wengel et al. |
| 7,105,294 B2 | | 9/2006 | Van Dongen et al. |
| 7,329,491 B2 | | 2/2008 | Kirchgesser et al. |
| 7,374,945 B2 | | 5/2008 | Becker |
| 7,572,582 B2 | | 8/2009 | Wengel et al. |
| 7,655,422 B2 | | 2/2010 | Adler et al. |
| 7,750,208 B2 | | 7/2010 | Huang et al. |
| 7,867,443 B2 | | 1/2011 | Key et al. |
| 7,901,634 B2 | | 3/2011 | Testa et al. |
| 8,034,909 B2 | | 10/2011 | Wengel et al. |
| 8,080,644 B2 | | 12/2011 | Wengel et al. |
| 8,153,365 B2 | | 4/2012 | Wengel et al. |
| 8,211,385 B2 | | 7/2012 | Testa et al. |
| 8,632,739 B2 | | 1/2014 | Winther et al. |
| 8,877,144 B2 | | 11/2014 | Poulsen et al. |
| 9,133,507 B2 | | 9/2015 | Testa et al. |
| 9,182,323 B2 | | 11/2015 | Poulsen et al. |
| 9,297,035 B2 | | 3/2016 | Matthiesen et al. |
| 9,303,287 B2 | | 4/2016 | Matthiesen |
| 9,309,562 B2 | | 4/2016 | Matthiesen |
| 9,388,456 B2 | | 7/2016 | Matthiesen |
| 9,388,466 B2 | | 7/2016 | Chen et al. |
| 10,202,638 B2 | | 2/2019 | Matthiesen |
| 10,662,465 B2 | | 5/2020 | Matthiesen |
| 2001/0000487 A1 | | 4/2001 | Essenfeld et al. |
| 2001/0007748 A1 | | 7/2001 | An et al. |
| 2001/0009766 A1 | | 7/2001 | Bard et al. |
| 2001/0010936 A1 | | 8/2001 | Richards et al. |
| 2001/0011131 A1 | | 8/2001 | Luyten et al. |
| 2001/0018512 A1 | | 8/2001 | Blanchard |
| 2001/0026919 A1 | | 10/2001 | Chenchik et al. |
| 2001/0027567 A1 | | 10/2001 | Federoff |
| 2001/0056203 A1 | | 12/2001 | Sezi et al. |
| 2002/0006652 A1 | | 1/2002 | Danielsen et al. |
| 2002/0019001 A1 | | 2/2002 | Light |
| 2002/0058278 A1 | | 5/2002 | Stefano et al. |
| 2002/0065224 A1 | | 5/2002 | Bender et al. |
| 2002/0076809 A1 | | 6/2002 | Steinmeyer et al. |
| 2002/0119465 A1 | | 8/2002 | Zhao et al. |
| 2002/0127569 A1 | | 9/2002 | Weisburg et al. |
| 2002/0150904 A1 | | 10/2002 | Bi et al. |
| 2002/0164589 A1 | | 11/2002 | Taylor |
| 2002/0164614 A1 | | 11/2002 | Becker |
| 2002/0182613 A1 | | 12/2002 | Mirkin et al. |
| 2002/0197629 A1 | | 12/2002 | Gjerde |
| 2002/0198366 A1 | | 12/2002 | Ashkenazi et al. |
| 2003/0108903 A1 | | 6/2003 | Wang et al. |
| 2003/0125312 A1 | | 7/2003 | Rocha et al. |
| 2003/0134279 A1 | | 7/2003 | Isola et al. |
| 2003/0175852 A1 | | 9/2003 | Kalra et al. |
| 2003/0203391 A1 | | 10/2003 | Sana et al. |
| 2004/0029184 A1 | | 2/2004 | Gourevitch |
| 2004/0030093 A1 | | 2/2004 | Sakurai et al. |
| 2004/0048376 A1 | * | 3/2004 | Chabot et al. ................ 435/455 |
| 2004/0053222 A1 | | 3/2004 | Storhoff et al. |
| 2004/0096856 A1 | | 5/2004 | Garimella et al. |
| 2004/0096967 A1 | | 5/2004 | Gryseels et al. |
| 2004/0101946 A1 | | 5/2004 | Hovanec |
| 2004/0106109 A1 | | 6/2004 | Belly et al. |
| 2004/0122101 A1 | | 6/2004 | Miller et al. |
| 2004/0210967 A1 | | 10/2004 | Chen et al. |
| 2004/0219546 A1 | | 11/2004 | Sakaki et al. |
| 2004/0224343 A1 | | 11/2004 | Han et al. |
| 2004/0241666 A1 | | 12/2004 | Amorese et al. |
| 2004/0248790 A1 | | 12/2004 | Hinuma et al. |
| 2004/0268439 A1 | | 12/2004 | Cheng et al. |
| 2005/0014154 A1 | | 1/2005 | Weizenegger |
| 2005/0064472 A1 | | 3/2005 | Shekar et al. |
| 2005/0079535 A1 | | 4/2005 | Kirchgesser et al. |
| 2005/0191657 A1 | | 9/2005 | Demorest et al. |
| 2005/0234236 A1 | | 10/2005 | Kertesz et al. |
| 2005/0250094 A1 | | 11/2005 | Storhoff et al. |
| 2005/0266459 A1 | * | 12/2005 | Poulsen ................... B82Y 5/00 |
| | | | 435/5 |
| 2006/0024751 A1 | | 2/2006 | May et al. |
| 2006/0030541 A1 | | 2/2006 | Garcia et al. |
| 2006/0040293 A1 | | 2/2006 | Salonen et al. |
| 2006/0147957 A1 | | 7/2006 | Qian et al. |
| 2006/0148846 A1 | | 7/2006 | Orwat et al. |
| 2006/0191657 A1 | | 8/2006 | Spence et al. |
| 2007/0141583 A1 | | 6/2007 | Li et al. |
| 2007/0148657 A1 | | 6/2007 | Myerson et al. |
| 2007/0166641 A1 | | 7/2007 | Shimizu et al. |
| 2007/0207482 A1 | | 9/2007 | Church et al. |
| 2007/0243545 A1 | | 10/2007 | Kilpatrick et al. |
| 2008/0044385 A1 | | 2/2008 | Nishi et al. |

(56) References Cited

U.S. PATENT DOCUMENTS

| | | |
|---|---|---|
| 2008/0050393 A1 | 2/2008 | Tang et al. |
| 2008/0076923 A1 | 3/2008 | Belogi et al. |
| 2008/0096262 A1 | 4/2008 | Kobayashi et al. |
| 2008/0108810 A1 | 5/2008 | Kertesz et al. |
| 2008/0188575 A1 | 8/2008 | Gaspar Martinho et al. |
| 2008/0220451 A1 | 9/2008 | Adler et al. |
| 2008/0227653 A1 | 9/2008 | Fodor et al. |
| 2008/0234474 A1 | 9/2008 | Braman et al. |
| 2008/0269502 A1 | 10/2008 | Gantz et al. |
| 2008/0318226 A1 | 12/2008 | Usui et al. |
| 2009/0123913 A1 | 5/2009 | Barany et al. |
| 2009/0197346 A1 | 8/2009 | Winkler et al. |
| 2009/0221429 A1 | 9/2009 | Fujimoto et al. |
| 2009/0294305 A1 | 12/2009 | Bekki et al. |
| 2010/0047671 A1 | 2/2010 | Chiang et al. |
| 2010/0136542 A1 | 6/2010 | Lee et al. |
| 2010/0196902 A1 | 8/2010 | Pestano et al. |
| 2010/0243451 A1 | 9/2010 | Latham et al. |
| 2010/0279283 A1 | 11/2010 | Raghunath et al. |
| 2011/0250698 A1 | 10/2011 | Pollner et al. |
| 2011/0262930 A1 | 10/2011 | Deleersnijder et al. |
| 2011/0281263 A1 | 11/2011 | Matthiesen et al. |
| 2011/0287951 A1 | 11/2011 | Emmert-Buck et al. |
| 2012/0331587 A1 | 12/2012 | Lassen et al. |
| 2013/0017176 A1 | 1/2013 | Hosoda et al. |
| 2013/0040294 A1 | 2/2013 | Matthiesen |
| 2013/0072535 A1 | 3/2013 | Stierli et al. |
| 2013/0156695 A1 | 6/2013 | Sprecher et al. |
| 2013/0230918 A1 | 9/2013 | Wakamiya |
| 2014/0017704 A1 | 1/2014 | Casta et al. |
| 2014/0242589 A1 | 8/2014 | Matthiesen |
| 2017/0283805 A1 | 10/2017 | Bonci et al. |
| 2019/0249235 A1 | 8/2019 | Matthiesen |
| 2020/0232018 A1 | 7/2020 | Matthiesen |
| 2020/0299769 A1 | 9/2020 | Matthiesen |

FOREIGN PATENT DOCUMENTS

| | | |
|---|---|---|
| EP | 1013772 | 6/2000 |
| WO | WO 91/02088 | 2/1991 |
| WO | 9204341 A1 | 3/1992 |
| WO | 9207956 A1 | 5/1992 |
| WO | WO 92/07959 | 5/1992 |
| WO | WO 94/02638 | 2/1994 |
| WO | WO 94/02639 | 2/1994 |
| WO | WO 96/04000 | 2/1996 |
| WO | 9927103 A1 | 6/1999 |
| WO | WO 99/14226 | 6/1999 |
| WO | 0006773 A1 | 2/2000 |
| WO | WO 00/69899 | 11/2000 |
| WO | WO 01/66804 | 9/2001 |
| WO | WO 02/061137 | 8/2002 |
| WO | 02088396 A2 | 11/2002 |
| WO | WO 03/014398 | 2/2003 |
| WO | WO 03/027328 | 4/2003 |
| WO | WO 03/054209 | 7/2003 |
| WO | WO 2006/007841 | 1/2006 |
| WO | 2006023919 A2 | 3/2006 |
| WO | WO 2006/066039 | 6/2006 |
| WO | 2006093150 A1 | 9/2006 |
| WO | WO 2006/117596 | 11/2006 |
| WO | WO 2007/058326 | 11/2006 |
| WO | 2007019432 A2 | 2/2007 |
| WO | 2007019492 A2 | 2/2007 |
| WO | 2007037314 A1 | 4/2007 |
| WO | 2007037341 A1 | 4/2007 |
| WO | 2007109441 A2 | 9/2007 |
| WO | WO 2007/109941 | 9/2007 |
| WO | WO 2009/074154 | 6/2009 |
| WO | 2009144561 A2 | 12/2009 |
| WO | WO 2009/144581 | 12/2009 |
| WO | WO 2009/147537 | 12/2009 |
| WO | 2010097655 A1 | 9/2010 |
| WO | 2010097656 A1 | 9/2010 |
| WO | 2010097707 A1 | 9/2010 |
| WO | 2011067678 A2 | 6/2011 |
| WO | 2011153354 A1 | 12/2011 |

OTHER PUBLICATIONS 2-pyrrolidone, Wikapedia Webpage, Nov. 1, 2012 (1 page).
Beebe, "Glycerin Antigen Retrieval," Microscopy Today, 9:30-31, 1999 (3 pages).
Boehringer Mannheim Biochemicals catalogue, "Nucleic Acid Hybridization—General Aspects," pp. 14-17 Jan. 1, 1992 (4 pages).
Brown et al., Analysis of RNA by Northern and Slot Blot Hybridization, Current Protocols in Molecular Biology, Unit 4.9 (19 pages).
DOW Ethylene Glycols, Webpage, Jun. 28, 2012 (2 pages).
DOW Propylene Glycol, Webpage, Jun. 28, 2012 (2 pages).
Extended European Search Report from the European Patent Office for corresponding EP Application No. 13164099.7, dated Aug. 14, 2013 (5 pages).
Extended European Search Report from the European Patent Office for corresponding EP Application No. 13164094.8, dated Aug. 8, 2013 (5 pages).
Hayat, editor, "Factors Affecting Antigen Retrieval," Chapter 4 of Microscopy, Immunohistochemistry and Antigen Retrieval, New York, p. 71-93, 2002 (23 pages).
International Search Report dated Jun. 16, 2008 for International Application No. PCT/DK2008/000066 (3 pages).
International Search Report and Written Opinion dated Sep. 22, 2009 for International Application No. PCT/IB2009/005893 (14 pages).
International Search Report and Written Opinion dated Feb. 15, 2010 for International Application No. PCT/IB2009/006548 (14 pages).
International Search Report and Written Opinion dated May 7, 2010 for International Application No. PCT/IB2009/007725 (18 pages).
International Search Report and Written Opinion dated Apr. 28, 2010 for International Application No. PCT/IB2009/007917 (15 pages).
International Search Report and Written Opinion dated Jul. 12, 2010 for International Application No. PCT/IB2010/00659 (16 pages).
Kurreck, "Improvement through novel chemical modifications," *Eur. J. Biochem.*, 270:1628-1644, 2003 (17 pages).
LyondellBassell, Webpage, Mar. 7, 2013 (1 page).
Markarian et al., "Effect of Diethylsulfoxide on the Thermal Denaturation of DNA," Department of Chemistry, Yerevan State University, Armenia, Jan. 19, 2006 (5 pages).
Moroni et al., "Gene copy number for epidermal growth factor receptor (EGFR) and clinical response to antiEGFR treatment in colorectal cancer: a cohort study," *Lancet Oncol.*, 6:279-286, 2005 (8 pages).
Notice of Allowance, Examiner-Initiated Interview Summary, and Reasons for Allowability, dated Feb. 20, 2013, in U.S. Appl. No. 12/526,323 (filed Feb. 16, 2010) (10 pages).
Nielsen et al., "PNA suppression method combined with fluorescence in situ hybridization (FISH) technique," Chapter 10 of PRINS and PNA Technologies in Chromosomal Investigation (Ed. Franck Pellestor), 2006 (22 pages).
Office Action, dated Jul. 17, 2012, in U.S. Appl. No. 12/526,323, filed Feb. 16, 2010) (16 pages).
Office Action dated Nov. 6, 2012, in U.S. Appl. No. 12/994,495, filed May 2011) (20 pages).
Office Action dated Mar. 18, 2013, in U.S. Appl. No. 13/203,149, filed Aug. 2011) (16 pages).
Office Action dated May 6, 2013, in U.S. Appl. No. 12/994,495, filed May 23, 2011) (17 pages).
Office Action, dated Oct. 4, 2013, in U.S. Appl. No. 13/203,149 (19 pages).
Office Action, dated Dec. 13, 2013, in U.S. Appl. No. 12/994,495 (26 pages).
Office Action, dated Feb. 20, 2013, in U.S. Appl. No. 12/526,323 (10 pages).

(56) References Cited

OTHER PUBLICATIONS

Office Action, dated Sep. 18, 2013, in U.S. Appl. No. 13/203,137 (33 pages).
Office Action, dated Sep. 24, 2013, in U.S. Appl. No. 13/203,160 (31 pages).
Olsen et al., "Amplification of HER2 and TOP2A and deletion of TOP2A genes in breast cancer investigated by new FISH probes," *Acta Oncologia* 43(1):35, 2004 (8 pages).
Optim synthetic Glycerine—Vapor Pressure and Boiling Point, Webpage, Jun. 28, 2012 (1 page).
Powell et al., "Metallographic in situ hybridization," Human Pathol., 38:1145-1159, 2007 (15 pages).
Shapiro et al., "Detection of N-myc gene amplification by fluorescence in situ hybridization," *Am. J. Pathology*, 145(5): 1339, 1993 (8 pages).
Stratagene Catalogue, p. 39, 1988 (2 pages).
Superscript™ First-Strand Synthesis System for RT-PCR, Invitrogen document dated Mar. 5, 2007 (4 pages).
Tkachuk et al., "Detection of bcr-abl fusion in Chronic Myelogenous Leukemia by in situ hybridization," *Science* 250:559, 1990 (4 pages).
Wahl, G. et al., "Efficient transfer of large DNA fragments from agarose gels to diazobenzyloxymethyl-paper and rapid hybridization by using dextran sulfate," *Proc. Natl. Acad. Sci.*, Aug. 1979, pp. 3683-3687, vol. 7, No. 8 (5 pages).
Woenckhause et al., "Multitarget FISH and LOH analysis at chromosome 3p in non-small cell lung cancer and adjacent bronchial epithelium," *Am. J. of Clin. Pathol.*, 123:752, 2005 (10 pages).
International Search Report for PCT/IB2009/005893, dated Sep. 22, 2009.
International Search Report for PCT/IB2009/006548, dated Feb. 15, 2010.
International Search Report for PCT/IB2009/007725, dated May 7, 2010.
International Search Report for PCT/IB2009/007917, dated Apr. 28, 2010.
International Search Report for PCT/IB2010/000659, dated Jul. 12, 2010.
Boehringer Mannheim Biochemicals Catalog, "Nucleic Acid Hybridization—General Aspects," pp. 14-17, Jan. 1, 1992.
Chakrabarti R. et al., "The enhancement of PCR amplification by low molecular-weight sulfones," Gene, 274:293-98 (2001).
Chakrabarti R. et al., "The enhancement of PCR amplification by low molecular weight amides," Nucleic Acids Research, 29(11):2377-81 (2001).
Chardonnet Y. et al., "Human papillomavirus detection in cervical cells by in situ hybridization with biotinylated probes," Cytopathology, 3(6):341-50 (1992).
Dako Catalog, "TOP2A FISH pharmDx™ Kit," pp. 1-33, May 24, 2007.
Luo H. et al., "Establishment of a simple and useful way for preimplantation genetic diagnosis of chromosomal diseases," Journal of Huazhong University of Science and Technology, 27(3):315-17 (2007).
Mochizuki S. et al., "Solvent effect on PCR from a viewpoint of a change of microscopic environment of Mg(2+) in a solution," Biochem Biophys Res Commun., Jun. 6, 2007 (Abstract only).
Nielsen K.V. et al., "PNA suppression method combined with fluorescence in situ hybridisation (FISH) technique," Chapter 10 in PRINS and PNA Technologies in Chromosomal Investigation (Ed. Franck Pellestor), 2006.
Olsen K.E. et al., "Amplification of HER2 and TOP2A and deletion of TOP2A genes in breast cancer investigated by new FISH probes," Acta Oncologica, 43(1):34-42 (2004).
EPO, "Request for Interpreters filed on Sep. 2, 2019", Application No. 12775027.1, 1 Page.
EPO, "Response to Brief Communication of Jan. 8, 2018 & Further to Notice of Opposition by Opponent filed on Jan. 26, 2018", Application No. 09754209.6, 4 Pages.
EPO, "Response to the Opponent's Letter of Feb. 1, 2018 filed on May 17, 2018", Application No. 13164094.8, 15 Pages.
EPO, "Summons to Attend Oral Proceedings mailed on Aug. 21, 2018", Application No. 09754209.6, 22 Pages.
EPO, "Summons to Attend Oral Proceedings mailed on Feb. 11, 2019", Application No. 12775027.1, 7 Pages.
EPO, "Summons to Attend Oral Proceedings mailed on May 22, 2018", Application No. 13164094.8, 37 Pages.
EPO, "Summons to Attend Oral Proceedings Received by Opponent mailed on Aug. 21, 2018", Application No. 39754209.6, 22 Pages.
EPO, "Summons to Attend Oral Proceedings Received by Opponent mailed on Feb. 11, 2019", Application No. 12775027.1, 7 Pages.
EPO, "Summons to Attend Oral Proceedings Received by Opponent mailed on May 22, 2018", Application No. 13164094.8, 37 Pages.
EPO, "Written Submission by Opponent in Preparation to/during Oral Proceedings filed on Apr. 27, 2019", Application No. 09754209.6, 17 Pages.
EPO, "Written Submission by Opponent in Preparation to/during Oral Proceedings Filed on Mar. 7, 2019", Application No. 09754209.6, 14 Pages.
EPO, "Written Submission by Opponent in Preparation to/during Oral Proceedings filed on Nov. 7, 2018", Application No. 13164094.8, 7 Pages.
EPO, "Written Submission by Opponent in Preparation to/during Oral Proceedings Filed on Sep. 4, 2019", Application No. 12775027.1, 6 Pages.
EPO, "Written Submission by Opponent in Preparation to/during Oral Proceedings filed on Sep. 28, 2018", Application No. 13164094.8, 9 Pages.
EPO, "Written Submission in Preparation to/during Oral Proceedings filed on Mar. 5, 2019", Application No. 39754209.6, 84 Pages.
EPO, "Written Submission in Preparation to/during Oral Proceedings filed on Nov. 22, 2018", Application No. 13164094.8, 123 Pages.
EPO, "Written Submission in Preparation to/during Oral Proceedings Filed on Sep. 4, 2019", Application No. 12775027.1, 107 Pages.
EPO, "Written Submission in Preparation to/during Oral Proceedings filed on Sep. 27, 2018", Application No. 13164094.8, 76 Pages.
Huber, et al., "Detection of Partial Denaturation in AT-Rich DNA Fragments by Ion-Pair Reserved-Phase Chromatography", Analytical Chemistry, vol. 68, No. 17, Sep. 1, 1996, 2959-2965.
INVITROGEN™, "Denhardt's Solution (50X)", Catalog No. 750018, ThermoFisher Scientific, 2007, 2 pages.
IUPAC Gold Book, "Glycols", Compendium of Chemical Terminology, 2nd ed. (the "Gold Book"). Compiled by A.D. McNaught and A. Wilkinson. Blackwell Scientific Publications, Oxford, 1997, 1 page.
IUPAC Gold Book, "Solution", Compendium of Chemical Terminology, 2nd ed. (the "Gold Book"). Compiled by A. D. McNaught and A. Wilkinson. Blackwell Scientific Publications, Oxford, 1997, 2 pages.
Kaye & Laby, "3.7.1 Dipole moments and dipole lengths", NPL(National Physical Laboratory) Kaye & Laby Tables of Physical & Chemical Constants, Mar. 23, 2008, 1-2.
Kiyama, et al., "In Situ Hybridization Method", New Genetic Engineering Handbook, Experimental Medical Edition, Muramatsu Masami, et al. Editors, Apr. 20, 1996, 202-203.
Launay, et al., "Hansen solubility parameters for a carbon fiber/epoxy composite", Carbon, vol. 45, No. 2859, 2007, 7 Pages.
Lawson, et al., "Dimethyl formamide-free, urea-NaCl fluorescence in situ hybridization assay for *Staphylococcus aureus*", Letters in Applied Microbiology, vol. 54, No. 263, 2011, 263-266.
Lyondellbasell, "N-Methy-2-Pyrrolidone", Application Data [retrieved on Mar. 7, 2013], Mar. 7, 2013, 4 pages.
Ma, et al., "Optimization of Hybridization Efficiency in cDNA Chip Technology", Acta Pharmaceutica Sinica, vol. 37, No. 2, 2002, 153-157.
Matthiesen, et al., "Fast and Non-Toxic In Situ Hybridization without Blocking of Repetitive Sequences", PLOS ONE, vol. 7, No. 7, Jul. 2012, e40675.

(56) References Cited

OTHER PUBLICATIONS

McAllister, et al., "In Situ Hybridization to Study the Origin and Fate of Identified Neurons", Science, vol. 222, No. 300, 1983, 800-808.
PCT, "International Search Report dated Jan. 14, 2013", International Application No. PCT/IB2012/002359, 4 pages.
PCT, "International Search Report dated Jun. 4, 2013", International Application No. PCT/EP2012/070877, 15 pages.
Rigby, et al., "Fluorescence In Situ Hybridization with Peptide Nucleic Acid Probes for Rapid Identifications of Candida Albicans Directly from Blood Culture Bottles", Journal of Clinical Microbiology, vol. 40, No. 6, Jun. 2002, 2182-2186.
Sassoon, et al., "Detection of Messenger RNA by in Situ Hybridization", Methods in Enzymology, Vo. 225, No. 384, 1993, 384-404.
Stender, et al., "Fluorescence In Situ Hybridization Assay Using Peptide Nucleic Acid Probes for Differentiation between Tuberculous and Nontuberculous Mycobacterium Species in Smears of Mycobacterium Cultures", Journal of clinical Microbiology, vol. 37, No. 9, Sep. 1999, 2760-2765.
Summersgill, et al., "Fluorescence and Chromogenic In Situ Hybridization to Detect Genetic Aberrations in Formalin-Fixed Paraffin Embedded Material, Including Tissue Microarrays", Nature Protocols, vol. 3, No. 2, Jan. 2008, 220-234.
The European Agency for the Eval, "2-Pyrrolidone", Summary Report, Committee for Veterinary Medical Products, Retrieved from the Internet: <URL: www.ema.europa.eu/docs/en_GB/document_library/Maximum_Residue_Limits_-_Report/2009/11/WC500015798.pdf>, Jul. 1998, 5 pages.
Toyozo, et al., "Principal Assay Method in Infection Diagnosis", Chapter 3. Diagnosis of Infection by DNA Probe, Applied DNA Probe Technology, Feb. 5, 1988, 36-39.
Wang, "Simultaneous Detection and Differentiation of *Staphylococcus* Species in Blood Cultures Using Fluorescence in situ Hybridization", Medical Principles and Practice, vol. 19, 2010, 218-221.
Wikipedia, "Solvent", Wikipedia, Apr. 17, 2019, 15 pages.
Wilkinson, et al., "Detection of Messenger RNA by in Situ Hybridization to Tissue Sections and Whole Mounts", Methods in Enzymology, vol. 225, No. 361, 1993, 361-373.
Xi, et al., "Use of DNA and Peptide Nucleic Acid Molecular Beacons for Detection and Quantification of rRNA in Solution and in Whole Cells", Applied and Environmental Microbiology, vol. 69, No. 9, Sep. 2003, 5673-5678.
EPO, "Brief Communication—Opposition Proceedings mailed on Oct. 16, 2017", Application No. 13164094.8, 67 Pages.
EPO, "Brief Communication—Opposition Proceedings mailed on Oct. 2, 2018", Application No. 12775027.1, 27 Pages.
EPO, "Brief Communication—Opposition Proceedings mailed on Oct. 5, 2018", Application No. 13164094.8, 77 Pages.
EPO, "Brief Communication—Opposition Proceedings mailed on Oct. 5, 2018", Application No. 13164094.8, 8 Pages.
EPO, "Brief Communication—Opposition Proceedings mailed on Sep. 6, 2019", Application No. 12775027.1, 2 Pages.
EPO, "Brief Communication—Opposition Proceedings mailed on Sep. 9, 2019", Application No. 12775027.1, 2 Pages.
EPO, "Brief Communication—Opposition Proceedings mailed on Sep. 12, 2019", Application No. 12775027.1, 6 Pages.
EPO, "Brief Communication—Opposition Proceedings mailed on Sep. 16, 2019", Application No. 12775027.1, 1 Page.
EPO, "Brief Communication of Jan. 8, 2018 of the EPO in the Opposition Proceedings Including the Aforementioned Document D14 (Termed "D5" in the Examination and Opposition Proceedings of EP 2285979) mailed on Feb. 7, 2018", Patent No. EP 2285979, 1 page.
EPO, "Communication of a Notice of Opposition—First Information to Patent Proprietor mailed on Apr. 24, 2018", Application No. 12775027.1, 1 Page.
EPO, "Communication of a Notice of Opposition—First Information to Patent Proprietor mailed on Apr. 26, 2017", Application No. 13164094.8, 1 Page.
EPO, "Communication of a Notice of Opposition—First Information to Patent Proprietor mailed on Oct. 20, 2017", Application No. 09754209.6, 1 Page.
EPO, "Communication of Further Notices of Opposition Pursuant to Rule 79(2) EPC mailed on Jan. 15, 2018", Application No. 09754209.6, 1 Page.
EPO, "Communication of Further Notices of Opposition Pursuant to Rule 79(2) EPC mailed on May 30, 2017", Application No. 13164094.8, 1 Page.
EPO, "Communication of Further Notices of Opposition Pursuant to Rule 79(2) EPC mailed on May 8, 2018", Application No. 12775027.1, 1 Page.
EPO, "Communication of Notices of Opposition (R. 79(1) EPC) mailed on Jan. 15, 2018", Application No. 39754209.6, 1 Page.
EPO, "Communication of Notices of Opposition (R. 79(1) EPC) mailed on May 30, 2017", Application No. 13164094.8, 1 Page.
EPO, "Communication of Notices of Opposition (R. 79(1) EPC) mailed on May 8, 2018", Application No. 12775027.1, 1 Page.
EPO, "Communication Pursuant to Rule 164(2)(b) and Article 94(3) EPC mailed on Jun. 12, 2015", Application No. 12775027.1, 6 pages.
EPO, "Communication Pursuant to Rule 82(2) EPC to Pay Printing Fees and File Translations mailed on Jul. 24, 2019", Application No. 13164094.8, 6 Pages.
EPO, "Communication to Opponent Concerning Maintenance mailed on Jul. 24, 2019", Application No. 13164094.8, 4 Pages.
EPO, "Electronic Versions of the Handwritten Amendments (Written Submission) submitted on Dec. 19, 2018", Application No. 13164094.8, 26 Pages.
EPO, "Electronic Versions of the Handwritten Amendments submitted on May 31, 2019", Application No. 09754209.6, 14 Pages.
EPO, "EPO Request for Documents Pursuant Rule 83 EPC/ Request for Translation Pursuant Rule 3(3) EPC to Opponent mailed on Oct. 20, 2017", Application No. 09754209.6, 1 Page.
EPO, "Extended European Search Report dated Jun 6, 2018", Application No. 18165184.5, 8 pages.
EPO, "Information About the Result of Oral Proceedings mailed on May 7, 2019", Application No. 09754209.6, 10 Pages.
EPO, "Information About the Result of Oral Proceedings mailed on Nov. 30, 2018", Application No. 13164094.8, 5 Pages.
EPO, "Interlocutory Decision in Opposition Proceedings (Art. 101(3)(a) and 106(2) EPC) mailed on Jul. 1, 2019", Application No. 09754209.6, 66 Pages.
EPO, "Interlocutory Decision in Opposition Proceedings (Art. 101(3)(a) and 106(2) EPC) mailed on Mar. 5, 2019", Application No. 13164094.8, 40 Pages.
EPO, "Internal Form—Opposition/Addressees mailed on Jul. 1, 2019", Application No. 09754209.6, 2 Pages.
EPO, "Internal Form—Opposition/Addressees mailed on Mar. 5, 2019", Application No. 13164094.8, 2 Pages.
EPO, "Maintenance of the Patent With the Documents Specified in the Final Decision mailed on Jul. 17, 2019", Application No. 13164094.8, 1 Page.
EPO, "Minutes of the Oral Proceedings (Opposition Division)—Conclusion of the Proceedings mailed on Mar. 5, 2019", Application No. 13164094.8, 3 Pages.
EPO, "Notice of Opposition by Opponent filed on Apr. 18, 2018", Application No. 12775027.1, 34 Pages.
EPO, "Notice of Opposition by Opponent filed on Apr. 20, 2017", Application No. 13164094.8, 37 Pages.
EPO, "Notice of Opposition by Opponent filed on Oct. 11, 2017", Application No. 09754209.6, 31 Pages.
EPO, "OPPODREX with Handwritten Amendments mailed on Jul. 1, 2019", Application No. 09754209.6, 39 Pages.
EPO, "OPPODREX with Handwritten Amendments mailed on Mar. 5, 2019", Application No. 13164094.8, 50 Pages.
EPO, "Patentees Letter of Oct. 15, 2015 in the Examination Proceedings", Application No. 12775027.1, 7 pages.
EPO, "Provision of the Minutes in Accordance with Rule 124(4) EPC mailed on Jul. 1, 2019", Application No. 09754209.6, 21 Pages.

(56) References Cited

OTHER PUBLICATIONS

EPO, "Provision of the Minutes in Accordance with Rule 124(4) EPC mailed on Mar. 5, 2019", Application No. 13164094.8, 25 Pages.
EPO, "Reply from the Opponent to Submission of Proprietor filed on Feb. 1, 2018", Application No. 13164094.8, 13 Pages.
EPO, "Reply of the Patent Proprietor to the Notice(s) of Opposition Filed on May 17, 2018", Application No. 09754209.6, 67 Pagess.
EPO, "Reply of the Patent Proprietor to the Notice(s) of Opposition filed on Oct. 6, 2017", Application No. 13164094.8, 66 Pages.
EPO, "Reply of the Patent Proprietor to the Notice(s) of Opposition filed on Sep. 18, 2018", Application No. 12775027.1, 26 pages.
EPO, "Request for Correction in Minutes of Oral Proceedings filed on Aug. 21, 2019", Application No. 09754209.6, 3 Pages.
EPO, "Request for Correction in Reference No. by Opponent filed on Jan. 23, 2018", Application No. 09754209.6, 3 Pages.
EPO, "Request for Documents Pursuant to Rule 83 EPC by Opponent filed on Jan. 2, 2018", Application No. 09754209.6, 3 Pages.
EPO, "Request for Interpreters by Opponent filed on Mar. 5, 2019", Application No. 09754209.6, 1 Page.
EPO, "Request for Interpreters by Opponent filed on Sep. 2, 2019", Application No. 12775027.1, 3 Pages.
Tsuruoka, M. et al.,"Rapid Hybridization at High Salt Concentration and Detection of Bacterial DNA Using Fluorescence Polarization," Combinatorial Chemistry & High Throughput Screening, 2003, vol. 6, No. 3, pp. 225-234.
Hansen, "Excerpt print version: Hansen solubility parameters, A User's Handbook", 2nd Edition, 2007.
Hitzeman, et al., "Dextran Sulfate as a Contaminant of DNA Extracted from Concentrated Viruses and as an Inhibiton of DNA Polymerases", Journal of Virology, vol. 27, No. 1, Jul. 1978, 255-257.
Acloque, et al., "In Situ Hybridization Analysis of Chick Embryos in Whole-Mount and Tissue Sections", Methods in Cell Biology, vol. 82, No. 169, 2008, 17 pages.
Ahern, "Biochemical, Reagents Kits Offer Scientists Good Return on Investment", The Scientist vol. 9, No. 15, Jul. 24, 1995, 20 pages.
Ahern, "DNA, RNA Probes Help Investigators Narrow the Search for Genes", The Scientist Magazine®, Nov. 27, 1995, 7 pages.
Berndt, et al., "Reduced Formamide Content and Hybridization Temperature Results in Increased Non-Radioactive MRNA In Situ Hybridization Signals", Acta Histochemica, vol. 98, No. 1, 1996, 79-87.
bioprotocols.info, "20X SSC Recipe", 20X SSC Buffer Recipe, SSC Buffer Preparation Protocol, Jul. 28, 2014, 1 page.
Burke, "Solubility Parameters: Theory and Application", The Book and Paper Group Annual, vol. 3, cool.conservation-us.org [retrieved on Feb. 12, 2014], 1984, 1-33.
Cox, et al., "Fluorescent DNA Hybridization Probe Preparation Using Amine Modification and Reactive Dye Coupling", BioTechniques, vol. 36, No. 1, Jan. 2004, 114-122.
Denny, et al., "Burkitt Lymphoma Cell Line Carrying a Variant Translocation Creates New DNA at the Breakpoint and Violates the Hierarchy of Immunoglobulin Gene Rearrangement", Molecular and Cellular Biology, vol. 5, No. 11, 1985, 3199.
EPO, "Acknowledgement of a Document (Opponent) mailed on Aug. 21, 2018", Application No. 09754209.6, 1 Page.
EPO, "Acknowledgement of a Document (Opponent) mailed on Feb. 11, 2019", Application No. 12775027.1, 1 Page.
EPO, "Acknowledgement of a Document (Opponent) mailed on Jul. 1, 2019", Application No. 09754209.6, 1 Page.
EPO, "Acknowledgement of a Document (Opponent) mailed on Mar. 5, 2019", Application No. 13164094.8, 1 Page.
EPO, "Acknowledgement of a Document (Opponent) mailed on May 22, 2018", Application No. 13164094.8, 1 Page.
EPO, "Acknowledgement of a Document mailed on Aug. 21, 2018", Application No. 09754209.6, 1 Page.
EPO, "Acknowledgement of a Document mailed on Feb. 11, 2019", Application No. 12775027.1, 1 Page.
EPO, "Acknowledgement of a Document mailed on Jul. 1, 2019", Application No. 09754209.6, 1 Page.
EPO, "Acknowledgement of a Document mailed on Mar. 5, 2019", Application No. 13164094.8, 1 Page.
EPO, "Acknowledgement of a Document mailed on May 22, 2018", Application No. 13164094.8, 1 Page.
EPO, "Advice of Delivery mailed on Aug. 23, 2018", Application No. 09754209.6, 1 Page.
EPO, "Advice of Delivery mailed on Aug. 24, 2018", Application No. 09754209.6, 1 Page.
EPO, "Advice of Delivery mailed on Aug. 27, 2018", Application No. 09754209.6, 2 Pages.
EPO, "Advice of Delivery mailed on Aug. 29, 2018", Application No. 09754209.6, 2 Pages.
EPO, "Advice of Delivery mailed on Feb. 13, 2019", Application No. 12775027.1, 1 Page.
EPO, "Advice of Delivery mailed on Feb. 15, 2019", Application No. 12775027.1, 1 Page.
EPO, "Advice of Delivery mailed on Feb. 26, 2019", Application No. 12775027.1, 1 Page.
EPO, "Advice of Delivery mailed on Jul. 3, 2019", Application No. 09754209.6, 1 Page.
EPO, "Advice of Delivery mailed on Jul. 8, 2019", Application No. 09754209.6, 2 Pages.
EPO, "Advice of Delivery mailed on Mar. 11, 2019", Application No. 13164094.8, 2 Pages.
EPO, "Advice of Delivery mailed on Mar. 6, 2019", Application No. 13164094.8, 1 Page.
EPO, "Advice of Delivery mailed on Mar. 8, 2019", Application No. 13164094.8, 1 Page.
EPO, "Advice of Delivery mailed on Mar. 8, 2019", Application No. 13164094.8, 2 Pages.
EPO, "Advice of Delivery mailed on May 24, 2018", Application No. 13164094.8, 1 Page.
EPO, "Advice of Delivery mailed on May 29, 2018", Application No. 13164094.8, 1 Page.
EPO, "Advice of Delivery mailed on May 29, 2018", Application No. 13164094.8, 2 Pages.
EPO, "Advice of Delivery mailed on May 30, 2018", Application No. 13164094.8, 2 Pages.
EPO, "Brief Communication—Opposition Proceedings mailed on Feb. 7, 2018", Application No. 13164094.8, 1 Pages.
EPO, "Brief Communication—Opposition Proceedings mailed on Jan. 7, 2019", Application No. 13164094.8, 27 Pages.
EPO, "Brief communication—Opposition Proceedings mailed on Jan. 8, 2018", Application No. 09754209.6, 3 Pages.
EPO, "Brief Communication—Opposition Proceedings mailed on Jul. 1, 2019", Application No. 09754209.6, 15 Pages.
EPO, "Brief Communication—Opposition Proceedings mailed on Mar. 11, 2019", Application No. 09754209.6, 2 Pages.
EPO, "Brief Communication—Opposition Proceedings mailed on Mar. 11, 2019", Application No. 09754209.6, 83 Pages.
EPO, "Brief Communication—Opposition Proceedings mailed on Mar. 13, 2019", Application No. 09754209.6, 23 Pages.
EPO, "Brief Communication—Opposition Proceedings mailed on May 2, 2018", Application No. 09754209.6, 4 Pages.
EPO, "Brief Communication—Opposition Proceedings mailed on May 25, 2018", Application No. 13164094.8, 16 Pages.
EPO, "Brief Communication—Opposition Proceedings mailed on May 25, 2018", Application No. 09754209.6, 64 Pages.
EPO, "Brief Communication—Opposition Proceedings mailed on May 3, 2019", Application No. 09754209.6, 51 Pages.
EPO, "Brief Communication—Opposition Proceedings mailed on Nov. 13, 2018", Application No. 13164094.8, 6 Pages.
EPO, "Brief Communication—Opposition Proceedings mailed on Nov. 30, 2018", Application No. 13164094.8, 126 Pages.
Brief Communication regarding Letter from Proprietor of Aug. 21, 2019—Opposition Proceedings mailed on Oct. 1, 2019, Application No. 09754209.6, 7 Pages.
Communication of Bibliographic Data mailed on Oct. 28, 2019, Application No. 09754209.6, 2 Pages.

(56) References Cited

OTHER PUBLICATIONS

Communication Pursuant to Rule 82(2) that Interlocutory Decision has become Final. mailed on Oct. 28, 2019, Application No. 09754209.6, 2 Pages.
Decision revoking the European patent mailed on Nov. 29, 2019, Application No. 12775027.1, 46 Pages.
Decision to maintain European Patent No. 2636756 mailed on Oct. 24, 2019, Application No. 13164094.8, 1 Page.
Information About the Result of Oral Proceedings mailed on Nov. 4, 2019, Application No. 12775027.1, 9 Pages.
Maintenance of the Patent with the Documents Specified in the Final Decision mailed on Oct. 17, 2019, Application No. 09754209.6, 1 Page.
Proprietor's Response to Communication Pursuant to Rule 82(2) EPC Filed on Oct. 11, 2019, Application No. 13164094.8, 19 pages.
Termination of the Opposition Proceedings with Maintenance of Patent mailed on Oct. 18, 2019, Application No. 13164094.8, 1 Page.
Written Submission by Opponent in Preparation to/during Oral Proceedings Filed on Oct. 30, 2019, Application No. 12775027.1, 10 Pages.
Winship, "An Improved Method for Directly Sequencing PCR Amplified Material Using Dimethyl Sulphoxide", Nucleic Acids Research, vol. 17, No. 3, 1989, 1266.
Gelfand, et al., "Thermostable DNA Polymerases", PCR Protocols: A Guide to Methods and Applications, Part One. Basic Methodology, 1990, 129-141.
Pernthaler, et al., "Fluorescence in Situ Hybridization (FISH) With rRNA-Targeted Oligonucleotide Probes", Methods in Microbiology vol. 30—Abstract Only, 2000, 207-210.
Powell, et al., "Rapid Confirmation of Single Copy Lambda Prophage Integration By PCR", Nucleic Acids Research, vol. 22, No. 25, 1994, 5765-5766.
Extended European Search Report dated Aug. 19, 2020, Application No. 20167307.6, 7 pages.
Hansen,Charles M. et al., Excerpt print version: Hansen solubility parameters, A User's Handbook, 2007.
Polyethylene glycol mono(4-tert-octylphenyl) ether. CAS Common Chemistry. CAS, a division of the American Chemical Society, n.d. https://commonchemistry.cas.org/detail?ref=9002-93-1 (retrieved Mar. 26, 2021) (CAS RN 9002-93-1), 4 pages.
Polyoxyethylene sorbitan monolaurate. CAS Common Chemistry. CAS, a division of the American Chemical Society, n.d. https://commonchemistry.cas.org/detail?ref=9005-64-5 (retrieved Mar. 26, 2021) (CAS RN: 9005-64-5), 5 pages.
Auxiliary Request 1 (Tracked & Clean) filed by Patentee on Dec. 18, 2020, EP Application No. 15184389.3, 12 pages.
Auxiliary Request 2 (Tracked & Clean) filed by Patentee on Dec. 18, 2020, EP Application No. 15184389.3, 12 pages.
Auxiliary Request 3 (Tracked & Clean) filed by Patentee on Dec. 18, 2020, EP Application No. 15184389.3, 12 pages.
Auxiliary Request 4 (Tracked & Clean) filed by Patentee on Dec. 18, 2020, EP Application No. 15184389.3, 12 pages.
Auxiliary Request 5 (Tracked & Clean) filed by Patentee on Dec. 18, 2020, EP Application No. 15184389.3, 12 pages.
Communication Re: Patentee Response to Opposition dated Jan. 11, 2021, EP Application No. 15184389.3, 47 pages.
Main Request (Tracked and Clean) filed by Patentee on Dec. 18, 2020, EP Application No. 15184389.3, 12 pages.
Patentee Response to Opposition filed on Dec. 18, 2020, EP Application No. 15184389.3, 45 pages.
Response to Patentee's Submission (dated Dec. 18, 2020) filed on Apr. 1, 2021, EP Application No. 15184389.3, 19 pages.
Summons to Oral Proceedings pursuant to Rule 115(1) EPC mailed on Apr. 8, 2021, EP Application No. 15184389.3, 25 Pages.
Polysorbate 20. (n.d.). In Wikipedia, last edited Feb. 17, 2021, https://en.wikipedia.org/wiki/Polysorbate_20, 3 pages.
Triton X-100. (n.d ). In Wikipedia, last edited Mar. 12, 2021, https://en.wikipedia.org/wiki/Triton_X-100, 4 pages.

\* cited by examiner

HYBRIDIZATION COMPOSITIONS AND METHODS

This application is a U.S. National Phase Application under 35 U.S.C. § 371 of PCT/IB2009/005893, filed May 27, 2009, which claims priority to U.S. Provisional Application No. 61/056,089, filed May 27, 2008, U.S. Provisional Application No. 61/155,683, filed Feb. 26, 2009, Danish Application No. PA 2008 00727, filed May 27, 2008, and Danish Patent Application No. PA 2009 00278, filed Feb. 27, 2009, all of which are incorporated herein by reference in their entireties.

FIELD OF THE INVENTION

The present invention relates to aqueous compositions for use in hybridization, for example, for use in in situ hybridization (ISH).

In one embodiment, the present invention relates to the field of molecular examination of DNA and RNA. In particular, the invention relates to the fields of cytology, histology, and molecular biology. In one aspect, the present invention relates to the energy (e.g., incubation time and heat) required during hybridization between nucleic acids, e.g., in in situ hybridization targeting DNA and RNA.

BACKGROUND AND DESCRIPTION

The double helix structure of DNA is stabilized by hydrogen bonding between bases on opposite strands when bases are paired in one particular way (A+T or G+C). This complementary base paring (hybridization) is central to all processes involving nucleic acids.

In a basic example of hybridization, nucleic acid fragments or sequences bind to a complementary nucleic acid fragment or sequence. For example, hybridization may use nucleic acid probes, designed to bind, or "hybridize," with a target, for example, DNA or RNA. One type of hybridization, in situ hybridization (ISH), includes hybridization to a target in a specimen wherein the specimen may be in vivo, or for example, fixed or adhered to a glass slide. The probes may be labeled to make identification of the probe-target hybrid possible by use of a fluorescence or bright field microscope/scanner. The fragment or sequence is typically a double or single stranded nucleic acid, such as a DNA, RNA, or analogs. In some embodiments, the fragment or sequence may be a probe that may be labeled using radioactive labels such as $^{31}$P, $^{33}$P, or $^{32}$S, non-radioactive labels such as digoxigenin and biotin, or fluorescent labels. Such labeled probes can be used to detect genetic abnormalities in a target sequence, providing valuable information about, e.g., prenatal disorders, cancer, and other genetic or infectious diseases.

The efficiency and accuracy of nucleic acid hybridization assays mostly depend on at least one of three major factors: a) denaturation (i.e., separation of, e.g., two nucleic acid strands) conditions, b) renaturation (i.e., re-annealing of, e.g., two nucleic acid strands) conditions, and c) post-hybridization washing conditions.

Traditional hybridization experiments, such as ISH assays, use a formamide-containing solution to denature doubled stranded nucleic acid. Formamide is a solvent that has a destabilizing effect on the helical state of, for example, DNA, RNA, and analogs by displacing loosely and uniformly bound hydrate molecules. Furthermore, formamide stabilizes the coil state of DNA, RNA, and analogs by 'formamidation' of the Watson-Crick binding sites of the bases. However, formamide is a toxic hazardous material, subject to strict regulations for use and waste.

Moreover, the use of formamide, while accepted as the standard technique for hybridization is hampered by the long time required to complete the hybridization, depending on the conditions and the nucleic acid fragments or sequences used. For example, the denaturation step is followed by a longer time-consuming hybridization step, which, e.g., in a traditional fluorescent in situ hybridization (FISH) protocol takes 14-24 hours, and can even take up to 72 hours. Examples of traditional hybridization times are shown in FIGS. 1 and 2.

The step of re-annealing (i.e., hybridizing) two complementary strands of nucleic acid chains is by far the most time-consuming aspect of an assay using hybridization. Until now it was believed that the use of chaotropic agents, such as formamide, guanidinium hydrogen, and urea, which interfere with the Watson-Crick binding sites of nucleic acid bases and thereby disturb the hydrogen bonds between complementary nucleic acid bases, was the only way to lower the melting temperature (Tm) of the complementary chains. However, although the use of chaotropic agents lowers the Tm, these agents appear to significantly prolong the hybridization time compared to hybridization in an aqueous solution without a chaotropic agent. Furthermore, besides the disadvantage of the long processing time, the use of a high concentration of formamide appears to incur morphological destruction of cellular, nuclear, and/or chromosomal structure. Finally, formamide is considered a toxic and hazardous chemical to humans.

The present invention provides several potential advantages over the prior art, such as faster hybridization times, lower hybridization temperatures, and less toxic hybridization solvents.

SUMMARY OF THE INVENTION

It is an object of the present invention to provide compositions which result in at least one of the following advantages: highly sensitive, technically easy, flexible and reliable hybridization procedures, and fast analyses. In some embodiments, for example, one advantage may be the ability to tailor the hybridization time by varying the temperature of the hybridization reaction to a much greater degree than is available using prior art methods. For example, hybridization may be possible at room temperature.

In one embodiment, the compositions and methods of the invention lower the energy necessary for hybridization. The compositions and methods of the invention are applicable to any hybridization technique. The compositions and methods of the invention are also applicable to any molecular system that hybridizes or binds using base pairing, such as, for example, DNA, RNA, PNA, LNA, and synthetic and natural analogs thereof.

It is a further object of the invention to provide hybridization methods and compositions that preserve the morphology of a biological sample. It is another object of the invention to provide a non-toxic hybridization composition and procedure. It is yet another object of the invention to provide a low evaporation hybridization technique. A further object of the invention is to provide a hybridization technique detectable with a 20× objective. Yet another object of the invention is to provide a composition with a low probe concentration. It is another object of the invention to reduce and/or remove the need for blocking of unspecific binding. The compositions and methods of the invention may also permit the use of heterogeneous probes without the need to block, remove, or otherwise disable the binding of, e.g., repetitive sequences in a biological sample.

In one embodiment, the nucleic acid hybridization method and compositions of the present invention are useful for the in vivo or in vitro analysis of genomic DNA, chromosomes, chromosome fragments, genes, and chromosome aberrations such as translocations, deletions, amplifications, insertions, mutations, or inversions associated with a normal condition or a disease. Further, the methods and compositions are useful for detection of infectious agents as well as changes in levels of expression of RNA, e.g., mRNA and its complementary DNA (cDNA).

Other uses include the in vivo or in vitro analysis of messenger RNA (mRNA), viral RNA, viral DNA, small interfering RNA (siRNA), small nuclear RNA (snRNA), noncoding RNA (ncRNA, e.g., tRNA and rRNA), transfer messenger RNA (tmRNA), micro RNA (miRNA), piwi-interacting RNA (piRNA), long noncoding RNA, small nucleolar RNA (snoRNA), antisense RNA, double-stranded RNA (dsRNA), methylations and other base modifications, single nucleotide polymorphisms (SNPs), copy number variations (CNVs), and nucleic acids labeled with, e.g., radioisotopes, fluorescent molecules, biotin, digoxigenin (DIG), or antigens, alone or in combination with unlabeled nucleic acids.

The nucleic acid hybridization method and compositions of the present invention are useful for in vivo or in vitro analysis of nucleic acids using techniques such as PCR, in situ PCR, northern blot, Southern blot, flow cytometry, autoradiography, fluorescence microscopy, chemiluminescence, immunohistochemistry, virtual karyotype, gene assay, DNA microarray (e.g., array comparative genomic hybridization (array CGH)), gene expression profiling, Gene ID, Tiling array, gel electrophoresis, capillary electrophoresis, and in situ hybridizations such as FISH, SISH, CISH. The methods and compositions of the invention may be used on in vitro and in vivo samples such as bone marrow smears, blood smears, paraffin embedded tissue preparations, enzymatically dissociated tissue samples, bone marrow, amniocytes, cytospin preparations, imprints, etc.

In one embodiment, the invention provides methods and compositions for hybridizing at least one molecule to a target. The invention may, for example, eliminate the use of, or reduce the dependence on formamide. For example, the methods and compositions of the invention may lower the energy barrier to hybridization without the use of formamide.

The lower energy barrier may reduce the time and or temperature necessary for hybridization. For example, the invention may allow for hybridization at lower temperatures or may allow for rapid hybridization at higher temperatures. Thus, in some aspects, the present invention overcomes a major time consuming step in hybridization assays.

One aspect of the invention is a composition or solution for use in hybridization. Compositions for use in the invention include an aqueous composition comprising at least one nucleic acid sequence and at least one polar aprotic solvent in an amount effective to denature double-stranded nucleotide sequences. An amount effective to denature double-stranded nucleotide sequences is an amount that enables hybridization. For example, one way to test for whether the amount of polar aprotic solvent is effective to enable hybridization is to determine whether the polar aprotic solvent, when used in the hybridization methods and compositions described herein, such as example 1, yield a detectable signal and/or an amplified nucleic acid product.

Non-limiting examples of effective amounts of polar aprotic solvents include, e.g., about 1% to about 95% (v/v). In some embodiments, the concentration of polar aprotic solvent is 5% to 60% (v/v). In other embodiments, the concentration of polar aprotic solvent is 10% to 60% (v/v). In still other embodiments, the concentration of polar aprotic solvent is 30% to 50% (v/v). Concentrations of 1% to 5%, 5% to 10%, 10%, 10% to 20%, 20% to 30%, 30% to 40%, 40% to 50%, or 50% to 60% (v/v) are also suitable. In some embodiments, the polar aprotic solvent will be present at a concentration of 0.1%, 0.25%, 0.5%, 1%, 2%, 3%, 4%, or 5% (v/v). In other embodiments, the polar aprotic solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

According to another aspect of the present invention the aqueous composition comprising a polar aprotic solvent has reduced toxicity. For example, a less-toxic composition than traditional hybridization solutions may comprise a composition with the proviso that the composition does not contain formamide, or with the proviso that the composition contains less than 10%, or less than 5%, or less than 2%, or less than 1%, or less than 0.5%, or less than 0.1%, or less than 0.05%, or less than 0.01% formamide. A less-toxic composition may also comprise a composition with the proviso that the composition does not contain dimethyl sulfoxide (DMSO), or with the proviso that the composition contains less than 10%, 5%, 2%, or less than 1%, or less than 0.5%, or less than 0.1%, or less than 0.05%, or less than 0.01% DMSO.

In one aspect of the invention, suitable polar aprotic solvents for use in the invention may be selected based on their Hansen Solubility Parameters. For example, suitable polar aprotic solvents may have a dispersion solubility parameter between 17.7 to 22.0 $MPa^{1/2}$, a polar solubility parameter between 13 to 23 $MPa^{1/2}$, and a hydrogen bonding solubility parameter between 3 to 13 $MPa^{1/2}$.

According to one aspect of the present invention, suitable polar aprotic solvents for use in the invention are cyclic compounds. A cyclic compound has a cyclic base structure. Examples include the cyclic compounds disclosed herein. In other embodiments, the polar aprotic solvent may be chosen from Formulas 1-4 below:

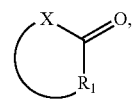

Formula 1

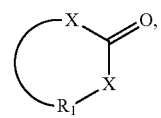

Formula 2

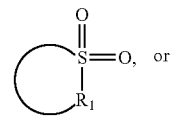

Formula 3

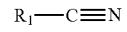

Formula 4 where X is O and $R_1$ is alkyldiyl.

According to another aspect of the invention, suitable polar aprotic solvents for use in the invention may be chosen from Formula 5 below:

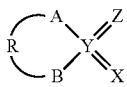

Formula 5 where X is optional and if present, is chosen from O or S;
where Z is optional and if present, is chosen from O or S;
where A and B independently are O or N or S or part of the alkyldiyl or a primary amine;
where R is alkyldiyl; and
where Y is O or S or C.

Examples of suitable polar aprotic solvents according to Formula 5 are provided in Formulas 6-9 below:

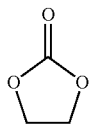

Formula 6 where:
X is non-existing;
A, B, and Z are O;
Y is C; and
R is Ethane-1,2 diyl;

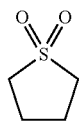

Formula 7 where:
Z and X are O;
A and B are part of the alkyldiyl;
Y is S; and
R is Butane-1,4 diyl;

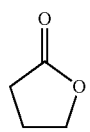

Formula 8 where:
X is non-existing;
A is part of the alkyldiyl;
Y is C;
B and Z is O; and
R is Propane-1,3 diyl;

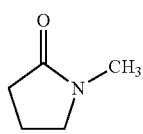

Formula 9 where:
X is non-existing;
A is part of the alkyldiyl;
Y is C;
B is methylamine;
Z is O; and
R is Propane-1,3 diyl;

According to yet another aspect of the invention the polar aprotic solvent has lactone, sulfone, nitrile, sulfite, or carbonate functionality. Such compounds are distinguished by their relatively high dielectric constants, high dipole moments, and solubility in water.

According to another aspect of the invention the polar aprotic solvent having lactone functionality is γ-butyrolactone (GBL), the polar aprotic solvent having sulfone functionality is sulfolane (SL), the polar aprotic solvent having nitrile functionality is acetonitrile (AN), the polar aprotic solvent having sulfite functionality is glycol sulfite/ethylene sulfite (GS), and the polar aprotic solvent having carbonate functionality is ethylene carbonate (EC), propylene carbonate (PC), or ethylene thiocarbonate (ETC).

According to yet another aspect, the invention discloses a method of hybridizing nucleic acid sequences comprising:
providing a first nucleic acid sequence,
providing a second nucleic acid sequence,
providing an aqueous composition comprising at least one polar aprotic solvent in an amount effective to denature double-stranded nucleotide sequences, and
combining the first and the second nucleic acid sequence and the aqueous composition for at least a time period sufficient to hybridize the first and second nucleic acid sequences.

In one embodiment, a sufficient amount of energy to hybridize the first and second nucleic acids is provided.

In one embodiment, the hybridization of the first nucleic acid sequence to the second nucleic acid sequence occurs in less than 8 hours, such as, for example, less than 6 hours, less than 5 hours, less than 4 hours, less than 3 hours, less than 2 hours, or less than 1 hour.

The method may, for example, comprise:
providing a first nucleic acid sequence, and
applying an aqueous composition comprising a second nucleic acid sequence and at least one polar aprotic solvent in an amount effective to denature double-stranded nucleotide sequences to said first nucleic acid sequence for at least a time period sufficient to hybridize the first and second nucleic acid sequences.

In one embodiment, a sufficient amount of energy to hybridize the first and second nucleic acids is provided.

In one embodiment, the hybridization of the first nucleic acid sequence to the second nucleic acid sequence occurs in less than 8 hours, such as, for example, less than 6 hours, less than 5 hours, less than 4 hours, less than 3 hours, less than 2 hours, or less than 1 hour.

According to yet another aspect of the present invention, the hybridization energy is provided by heating the aqueous composition and nucleic acid sequence. Thus, the step of hybridizing may include the steps of heating and cooling the aqueous composition and nucleic acid sequences.

According to another aspect of the invention, the denaturation and hybridization steps may occur separately. For example, the specimen may be denatured with a solution without probe and thereafter hybridized with probe.

A further aspect of the invention comprises a method wherein the step of providing a sufficient amount of energy to hybridize the nucleic acids involves a heating step performed by the use of microwaves, hot baths, hot plates, heat wire, peltier element, induction heating, or heat lamps.

According to another aspect the present invention relates to a method wherein the hybridization takes less than 1 hour. In other embodiments, the hybridization takes less than 30 minutes. In still other embodiments, the hybridization takes less than 15 minutes. In other embodiments, the hybridization takes less than 5 minutes.

According to a further aspect, the invention relates to the use of a composition comprising between 1 and 95% (v/v) of at least one polar aprotic solvent in hybridization assays.

According to yet another aspect, the invention relates to the use of a composition comprising an aqueous composition as described in this invention for use in hybridization assays.

DETAILED DESCRIPTION

A. Definitions

Figure 1:
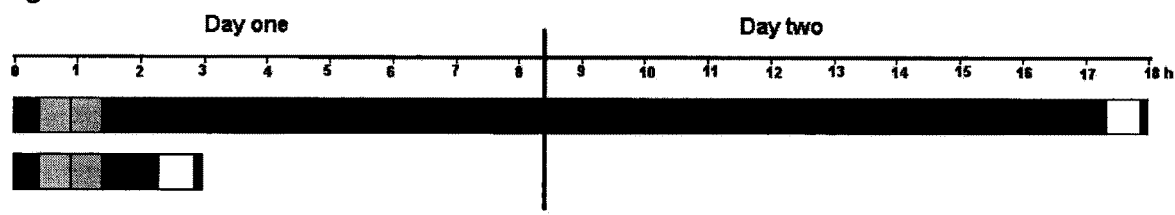
FIG. 1 depicts a typical time-course for single locus detection with primary labeled FISH probes on formaldehyde fixed paraffin embedded tissue sections (histological specimens). The bars represent a hybridization performed using a traditional solution (top) and a typical time-course for a hybridization performed using a composition of the invention (bottom). The first bar on the left in each time-course represents the deparaffination step; the second bar represents the heat-pretreatment step; the third bar represents the digestion step; the fourth bar represents the denaturation and hybridization step; the fifth bar represents the stringency wash step; and the sixth bar represents the mounting step.

In the context of the present invention the following terms are to be understood as follows:

"Biological sample" is to be understood as any in vivo, in vitro, or in situ sample of one or more cells or cell fragments. This can, for example, be a unicellular or multicellular organism, tissue section, cytological sample, chromosome spread, purified nucleic acid sequences, artificially made nucleic acid sequences made by, e.g., a biologic based system or by chemical synthesis, microarray, or other form of nucleic acid chip. In one embodiment, a sample is a mammalian sample, such as, e.g., a human, murine, rat, feline, or canine sample.

"Nucleic acid," "nucleic acid chain," and "nucleic acid sequence" mean anything that binds or hybridizes using base pairing including, oligomers or polymers having a backbone formed from naturally occurring nucleotides and/or nucleic acid analogs comprising nonstandard nucleobases and/or nonstandard backbones (e.g., a peptide nucleic acid (PNA) or locked nucleic acid (LNA)), or any derivatized form of a nucleic acid.

As used herein, the term "peptide nucleic acid" or "PNA" means a synthetic polymer having a polyamide backbone with pendant nucleobases (naturally occurring and modified), including, but not limited to, any of the oligomer or polymer segments referred to or claimed as peptide nucleic acids in, e.g., U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470, 6,201,103, 6,228,982 and 6,357,163, WO96/04000, all of which are herein incorporated by reference, or any of the references cited therein. The pendant nucleobase, such as, e.g., a purine or pyrimidine base on PNA may be connected to the backbone via a linker such as, e.g., one of the linkers taught in PCT/US02/30573 or any of the references cited therein. In one embodiment, the PNA has an N-(2-aminoethyl)-glycine) backbone. PNAs may be synthesized (and optionally labeled) as taught in PCT/US02/30573 or any of the references cited therein. PNAs hybridize tightly, and with high sequence specificity, with DNA and RNA, because the PNA backbone is uncharged. Thus, short PNA probes may exhibit comparable specificity to longer DNA or RNA probes. PNA probes may also show greater specificity in binding to complementary DNA or RNA.

As used herein, the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon. See generally, Kurreck, Eur. J. Biochem., 270:1628-44 (2003).

Examples of nucleic acids and nucleic acid analogs also include polymers of nucleotide monomers, including double and single stranded deoxyribonucleotides (DNA), ribonucleotides (RNA), α-anomeric forms thereof, synthetic and natural analogs thereof, and the like. The nucleic acid chain may be composed entirely of deoxyribonucleotides, ribonucleotides, peptide nucleic acids (PNA), locked nucleic acids (LNA), synthetic or natural analogs thereof, or mixtures thereof. DNA, RNA, or other nucleic acids as defined herein can be used in the method and compositions of the invention.

"Polar aprotic solvent" refers to an organic solvent having a dipole moment of about 2 debye units or more, a water solubility of at least about 5% (volume) at or near ambient temperature, i.e., about 20° C., and which does not undergo significant hydrogen exchange at approximately neutral pH, i.e., in the range of 5 to 9, or in the range 6 to 8. Polar aprotic solvents include those defined according to the Hansen Solubility Parameters discussed below.

"Alkyldiyl" refers to a saturated or unsaturated, branched, straight chain or cyclic hydrocarbon radical having two monovalent radical centers derived by the removal of one hydrogen atom from each of two different carbon atoms of a parent alkane, alkene, or alkyne.

"Aqueous solution" is to be understood as a solution containing water, even small amounts of water. For example, a solution containing 1% water is to be understood as an aqueous solution.

"Hybridization" is to be understood to incorporate both the denaturation and re-annealing steps of the hybridization procedure unless otherwise specified.

"Hybridization composition" refers to an aqueous solution of the invention for performing a hybridization procedure, for example, to bind a probe to a nucleic acid sequence. Hybridization compositions may comprise, e.g., at least one polar aprotic solvent, at least one nucleic acid sequence, and a hybridization solution. Hybridization compositions do not comprise enzymes or other components, such as deoxynucleoside triphosphates (dNTPs), for amplifying nucleic acids in a biological sample.

"Hybridization solution" refers to an aqueous solution for use in a hybridization composition of the invention. Hybridization solutions are discussed in detail below and may comprise, e.g., buffering agents, accelerating agents, chelating agents, salts, detergents, and blocking agents.

"PCR composition" refers to an aqueous solution of the invention for performing a hybridization procedure to amplify a nucleic acid sequence. PCR compositions may comprise, e.g., at least one polar aprotic solvent, at least one enzyme for amplifying nucleic acids, a set of nucleic acid oligonucleotide primers, a mixture of dNTPs, and a PCR solution.

"PCR solution" refers to an aqueous solution for use in a PCR composition of the invention. PCR solutions may comprise e.g., buffering agents, accelerating agents, chelating agents, salts, and detergents.

"Hansen Solubility Parameters" and "HSP" refer to the following cohesion energy (solubility) parameters: (1) the dispersion solubility parameter ($\delta_D$, "D parameter"), which measures nonpolar interactions derived from atomic forces; (2) the polar solubility parameter ($\delta_P$, "P parameter"), which measures permanent dipole-permanent dipole interactions; and (3) the hydrogen bonding solubility parameter ($\delta_H$, "H parameter"), which measures electron exchange. The Hansen Solubility Parameters are further defined below.

"Repetitive Sequences" is to be understood as referring to the rapidly reannealing (approximately 25%) and/or intermediately reannealing (approximately 30%) components of mammalian genomes. The rapidly reannealing components contain small (a few nucleotides long) highly repetitive sequences usually found in tandem (e.g., satellite DNA), while the intermediately reannealing components contain interspersed repetitive DNA. Interspersed repeated sequences are classified as either SINEs (short interspersed repeat sequences) or LINEs (long interspersed repeated sequences), both of which are classified as retrotransposons in primates. SINEs and LINEs include, but are not limited to, Alu-repeats, Kpn-repeats, di-nucleotide repeats, tri-nucleotide repeats, tetra-nucleotide repeats, penta-nucleotide repeats and hexa-nucleotide repeats. Alu repeats make up the majority of human SINEs and are characterized by a consensus sequence of approximately 280 to 300 bp that consist of two similar sequences arranged as a head to tail dimer. In addition to SINEs and LINEs, repeat sequences also exist in chromosome telomeres at the termini of chromosomes and chromosome centromeres, which contain distinct repeat sequences that exist only in the central region of a chromosome. However, unlike SINEs and LINEs, which are dispersed randomly throughout the entire genome, telomere and centromere repeat sequences are localized within a certain region of the chromosome.

"Non-toxic" and "reduced toxicity" are defined with respect to the toxicity labeling of formamide according to "Directive 1999/45/EC of the European Parliament and of the Council of 31 May 1999 concerning the approximation of the laws, regulations and administrative provisions of the Member States relating to the classification, packaging, and labelling of dangerous preparations" (ecb.jrc.it/legislation/1999L0045EC.pdf) ("Directive"). According to the Directive, toxicity is defined using the following classification order: T+"very toxic"; T "toxic", C "corrosive", Xn "harmful", Xi "irritant." Risk Phrases ("R phrases") describe the risks of the classified toxicity. Formamide is listed as T (toxic) and R61 (may cause harm to the unborn child). All of the following chemicals are classified as less toxic than formamide: acetonitrile (Xn, R11, R20, R21, R22, R36); sulfolane (Xn, R22); γ-butyrolactone (Xn, R22, R32); and ethylene carbonate (Xi, R36, R37, R38). At the time of filing this application, ethylene trithiocarbonate and glycol sulfite are not presently labeled.

B. Solvent Selection

Suitable polar aprotic solvents for use in the invention may be selected based on their Hansen Solubility Parameters. Methods for experimentally determining and/or calculating HSP for a solvent are known in the art, and HSP have been reported for over 1200 chemicals.

For example, the D parameter may be calculated with reasonable accuracy based on refractive index, or may be derived from charts by comparison with known solvents of similar size, shape, and composition after establishing a critical temperature and molar volume. The P parameter may be estimated from known dipole moments (see, e.g., McClellan A. L., Tables of Experimental Dipole Moments (W.H. Freeman 1963)) using Equation 1:

$$\delta_P = 37.4(\text{Dipole Moment})/V^{1/2} \qquad \text{Equation 1}$$

where V is the molar volume. There are no equations for calculating the H parameter. Instead, the H parameter is usually determined based on group contributions.

HSP characterizations are conveniently visualized using a spherical representation, with the HSP of an experimentally-determined suitable reference solvent at the center of the sphere. The radius of the sphere (R) indicates the maximum tolerable variation from the HSP of the reference solvent that still allows for a "good" interaction to take place. Good solvents are within the sphere and bad ones are outside. The distance, $R_a$, between two solvents based on their respective HSP values can be determined using Equation 2:

$$(R_a)^2 = 4(\delta_{D1} - \delta_{D2})^2 + (\delta_{P1} - \delta_{P2})^2(\delta_{H1} - \delta_{H2})^2 \qquad \text{Equation 2}$$

where subscript 1 indicates the reference sample, subscript 2 indicates the test chemical, and all values are in $\text{MPa}^{1/2}$. Good solubility requires that $R_a$ be less than the experimentally-determined radius of the solubility sphere $R_o$. The relative energy difference between two solvents, i.e., RED number, can be calculated by taking the ratio of $R_a$ to $R_o$, as shown in Equation 3.

$$\text{RED} = R_a/R_o \qquad \text{Equation 3}$$

RED numbers less than 1.0 indicate high affinity; RED numbers equal or close to 1.0 indicate boundary conditions; and progressively higher RED numbers indicate progressively lower affinities.

In some embodiments, the D parameters of the polar aprotic solvents of the invention are between 17.7 to 22.0 $\text{MPa}^{1/2}$. Such relatively high D parameters are generally associated with solvents having cyclic structures and/or structures with sulfur or halogens. Linear compounds are not likely to be among the most suitable polar aprotic solvents for use in the invention, but may be considered if their P and H parameters are within the ranges discussed below. Since the D parameter is multiplied by 4 in Equation 2, the limits are one-half of $R_o$. In addition, it should be noted that D values of around 21 or higher are often characteristic of a solid.

In some embodiments, the P parameters of the polar aprotic solvents of the invention are between 13 to 23 $\text{MPa}^{1/2}$. Such exceptionally high P parameters are generally associated with solvents having a high dipole moment and presumably also a relatively low molecular volume. For example, for V near 60 cc/mole, the dipole moment should be between 4.5 and 3.1. For V near 90 cc/mole, the dipole moment should be between 5.6 and 3.9.

In some embodiments, the H parameters of the polar aprotic solvents of the invention are between 3 to 13 $\text{MPa}^{1/2}$. Generally, polar aprotic solvents having an alcohol group are not useful in the compositions and methods of the invention, since the H parameters of such solvents would be too high.

The molar volume of the polar aprotic solvent may also be relevant, since it enters into the evaluation of all three Hansen Solubility Parameters. As molar volume gets smaller, liquids tend to evaporate rapidly. As molar volume gets larger, liquids tend to enter the solid region in the range of D and P parameters recited above. Thus, the polar aprotic solvents of the invention are rather close to the liquid/solid boundary in HSP space.

In some embodiments, the polar aprotic solvents of the invention have lactone, sulfone, nitrile, sulfite, and/or carbonate functionality. Such compounds are distinguished by their relatively high dielectric constants, high dipole moments, and solubility in water. An exemplary polar aprotic solvent with lactone functionality is γ-butyrolactone (GBL), an exemplary polar aprotic solvent with sulfone functionality is sulfolane (SL; tetramethylene sulfide-dioxide), an exemplary polar aprotic solvent with nitrile functionality is acetonitrile (AN), an exemplary polar aprotic solvent with sulfite functionality is glycol sulfite/ethylene sulfite (GS), and an exemplary polar aprotic solvents with carbonate functionality are ethylene carbonate (EC), propylene carbonate (PC), or ethylene trithiocarbonate (ETC). The structures of these exemplary solvents are provided below and their Hansen Solubility Parameters, RED numbers, and molar volumes are given in Table 1.

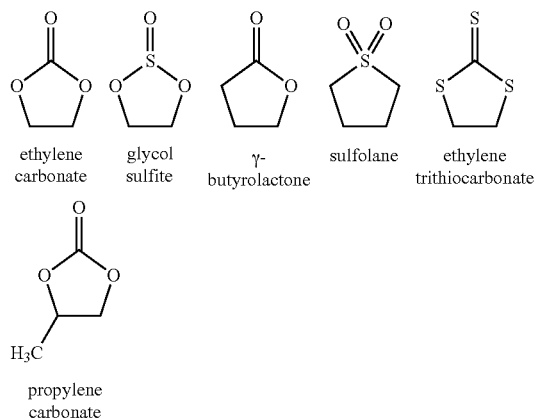

ethylene carbonate | glycol sulfite | γ-butyrolactone | sulfolane | ethylene trithiocarbonate propylene carbonate

TABLE 1

|  | D | P | H | RED | Molar Volume (cm$^3$/mole) |
|---|---|---|---|---|---|
| Correlation ($R_0$ = 3.9) | 19.57 | 19.11 | 7.71 | — | — |
| GBL | 19.0 | 16.6 | 7.4 | 0.712 | 76.5 |
| PC | 20.0 | 18.0 | 4.1 | 0.993 | 85.2 |
| SL | 20.3 | 18.2 | 10.9 | 0.929 | 95.7 |
| EC | 19.4 | 21.7 | 5.1 | 0.946 | 66.0 |
| ETC | n/a | n/a | n/a | n/a | n/a |
| GS | 20.0 | 15.9 | 5.1 | n/a | 75.1 | n/a = not available.

Other suitable polar aprotic solvents that may be used in the invention are cyclic compounds such as, e.g., ε-caprolactone. In addition, substituted pyrrolidinones and related structures with nitrogen in a 5- or 6-membered ring, and cyclic structures with two nitrile groups, or one bromine and one nitrile group, may also be suitable for use in the invention. For example, N-methylpyrrolidinone (shown below) may be a suitable polar aprotic solvent for use in the methods and compositions of the invention.

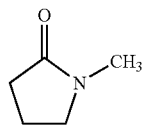

Other suitable polar aprotic solvents may contain a ring urethane group (NHCOO—). However, not all such compounds are suitable, since 1,3-dimethyl-2-imidazolidinone produces no signals when used in the hybridization compositions of the invention. One of skill in the art may screen for compounds useful in the compositions and methods of the invention as described herein. Exemplary chemicals that may be suitable for use in the invention are set forth in Tables 2 and 3 below.

TABLE 2

| Solvent | D | P | H |
|---|---|---|---|
| Acetanilide | 20.6 | 13.3 | 12.4 |
| N-Acetyl Pyrrolidone | 17.8 | 13.1 | 8.3 |
| 4-Amino Pyridine | 20.4 | 16.1 | 12.9 |
| Benzamide | 21.2 | 14.7 | 11.2 |
| Benzimidazole | 20.6 | 14.9 | 11.0 |
| 1,2,3-Benzotriazole | 18.7 | 15.6 | 12.4 |
| Butadienedioxide | 18.3 | 14.4 | 6.2 |
| 2,3-Butylene Carbonate | 18.0 | 16.8 | 3.1 |
| Caprolactone (Epsilon) | 19.7 | 15.0 | 7.4 |
| Chloro Maleic Anhydride | 20.4 | 17.3 | 11.5 |
| 2-Chlorocyclohexanone | 18.5 | 13.0 | 5.1 |
| Chloronitromethane | 17.4 | 13.5 | 5.5 |
| Citraconic Anhydride | 19.2 | 17.0 | 11.2 |
| Crotonlactone | 19.0 | 19.8 | 9.6 |
| Cyclopropylnitrile | 18.6 | 16.2 | 5.7 |
| Dimethyl Sulfate | 17.7 | 17.0 | 9.7 |
| Dimethyl Sulfone | 19.0 | 19.4 | 12.3 |
| Dimethyl Sulfoxide | 18.4 | 16.4 | 10.2 |
| 1,2-Dinitrobenzene | 20.6 | 22.7 | 5.4 |
| 2,4-Dinitrotoluene | 20.0 | 13.1 | 4.9 |
| Dipheynyl Sulfone | 21.1 | 14.4 | 3.4 |
| 1,2-Dinitrobenzene | 20.6 | 22.7 | 5.4 |
| 2,4-Dinitrotoluene | 20.0 | 13.1 | 4.9 |
| Epsilon-Caprolactam | 19.4 | 13.8 | 3.9 |
| Ethanesulfonylchloride | 17.7 | 14.9 | 6.8 |
| Furfural | 18.6 | 14.9 | 5.1 |
| 2-Furonitrile | 18.4 | 15.0 | 8.2 |
| Isoxazole | 18.8 | 13.4 | 11.2 |
| Maleic Anhydride | 20.2 | 18.1 | 12.6 |
| Malononitrile | 17.7 | 18.4 | 6.7 |
| 4-Methoxy Benzonitrile | 19.4 | 16.7 | 5.4 |
| 1-Methoxy-2-Nitrobenzene | 19.6 | 16.3 | 5.5 |
| 1-Methyl Imidazole | 19.7 | 15.6 | 11.2 |
| 3-Methyl Isoxazole | 19.4 | 14.8 | 11.8 |
| N-Methyl Morpholine-N-Oxide | 19.0 | 16.1 | 10.2 |
| Methyl Phenyl Sulfone | 20.0 | 16.9 | 7.8 |
| Methyl Sulfolane | 19.4 | 17.4 | 5.3 |
| Methyl-4-Toluenesulfonate | 19.6 | 15.3 | 3.8 |
| 3-Nitroaniline | 21.2 | 18.7 | 10.3 |
| 2-Nitrothiophene | 19.7 | 16.2 | 8.2 |
| 9,10-Phenanthrenequinone | 20.3 | 17.1 | 4.8 |
| Phthalic Anhydride | 20.6 | 20.1 | 10.1 |
| 1,3-Propane Sultone | 18.4 | 16.0 | 9.0 |
| beta-Propiolactone | 19.7 | 18.2 | 10.3 |
| 2-Pyrrolidone | 19.4 | 17.4 | 11.3 |
| Saccharin | 21.0 | 13.9 | 8.8 |
| Succinonitrile | 17.9 | 16.2 | 7.9 |
| Sulfanilamide | 20.0 | 19.5 | 10.7 |
| Sulfolane | 20.3 | 18.2 | 10.9 |
| 2,2,6,6-Tetrachlorocyclohexanone | 19.5 | 14.0 | 6.3 |
| Thiazole | 20.5 | 18.8 | 10.8 |
| 3,3,3-Trichloro Propene | 17.7 | 15.5 | 3.4 |
| 1,1,2-Trichloro Propene | 17.7 | 15.7 | 3.4 |
| 1,2,3-Trichloro Propene | 17.8 | 15.7 | 3.4 |

Table 2 sets forth an exemplary list of potential chemicals for use in the compositions and methods of the invention based on their Hansen Solubility Parameters. Other compounds, may of course, also meet these requirements. Some of these chemicals have been used in hybridization and/or PCR solutions in the prior art (e.g., dimethyl sulfoxide (DMSO) has been used in hybridization and PCR solutions, and sulfolane (SL) has been used in PCR solutions), but most have not. However, the prior art did not recognize that these compounds may be advantageously used to decrease hybridization times and/or temperatures, as disclosed in this application.

TABLE 3

| Chemical (dipole moment) | RED | Melting Point ° C. |
|---|---|---|
| Chloroethylene carbonate (4.02) | 0.92 | — |
| 2-Oxazolidinone (5.07) | 0.48 | 86-89 |
| 2-Imidazole | 1.49 | 90-91 |
| 1,5-Dimethyl Tetrazole (5.3) | ~1.5 | 70-72 |
| N-Ethyl Tetrazole (5.46) | ~1.5 | |
| Trimethylene sulfide-dioxide (4.49) | — | — |
| Trimethylene sulfite (3.63) | — | — |
| 1,3-Dimethyl-5-Tetrazole (4.02) | — | — |
| Pyridazine (3.97) | 1.16 | −8 |
| 2-Thiouracil (4.21) | — | — |
| N-Methyl Imidazole (6.2) | 1.28 | — |
| 1-Nitroso-2-pyrolidinone | ~1.37 | — |
| Ethyl Ethyl Phosphinate (3.51) | — | — |
| 5-cyano-2-Thiouracil (5.19) | — | — |
| 4H-Pyran-4-thione (4.08) | 1.35 | 32-34 |
| 4H-Pyran-4-one = gamma pyrone (4.08) | 1.49 | Boiling Point (BP) 80 |
| 2-Nitrofuran (4.41) | 1.14 | 29 |
| Methyl alpha Bromo Tetronate (6.24) | — | — |
| Tetrahydrothiapyran oxide (4.19) | 1.75 | 60-64 |
| Picolinonitrile (2-cyanopyridine) (5.23) | 0.40 | 26-28 (BP 212-215) |
| Nitrobenzimidazole (6.0) | 0.52 | 207-209 |
| Isatin (5.76) | — | 193-195 |
| N-phenyl sydnone (6.55) | — | — |
| Glycol sulfate (Ethylene glycol) | — | 99° C. |
| Note: not soluble at 40% | | |

Not all of the chemicals listed in Tables 2 and 3 are suitable for use in the compositions and methods of the invention. For example, although DMSO is listed in Table 2 because its Hansen Solubility Parameters (HSPs) fall within the ranges recited above, DMSO does not function to decrease hybridization times and/or temperatures in the compositions and methods of the invention. Thus, in some embodiments, the aqueous composition does not contain DMSO as a polar aprotic solvent. However, it is well within the skill of the ordinary artisan to screen for suitable compounds using the guidance provided herein including testing a compound in one of the examples provided. For example, in some embodiments, suitable polar aprotic solvents will have HSPs within the ranges recited above and a structure shown in Formulas 1-9 above.

C. Compositions, Buffers, and Solutions (1) Hybridization Solutions

Traditional hybridization solutions are known in the art. Such solutions may comprise, for example, buffering agents, accelerating agents, chelating agents, salts, detergents, and blocking agents.

For example, the buffering agents may include SSC, HEPES, SSPE, PIPES, TMAC, TRIS, SET, citric acid, a phosphate buffer, such as, e.g., potassium phosphate or sodium pyrophosphate, etc. The buffering agents may be present at concentrations from 0.5× to 50×. Typically, the buffering agents are present at concentrations from 2× to 10×.

The accelerating agents may include polymers such as FICOLL, PVP, heparin, dextran sulfate, proteins such as BSA, glycols such as ethylene glycol, glycerol, 1,3 propanediol, propylene glycol, or diethylene glycol, combinations thereof such as Dernhardt's solution and BLOTTO, and organic solvents such as formamide, dimethylformamide, DMSO, etc. The accelerating agent may be present at concentrations from 1% to 80% or 0.1× to 10×. Typically, formamide is present at concentrations from 25% to 75%, while DMSO, dextran sulfate, and glycol are present at concentrations from 5% to 10%.

The chelating agents may include EDTA, EGTA, etc. The chelating agents may be present at concentrations from 0.1 mM to 10 mM. Typically, the chelating agents are present at concentrations from 0.5 mM to 5 mM.

The salts may include sodium chloride, sodium phosphate, magnesium phosphate, etc. The salts may be present at concentrations from 1 mM to 750 mM. Typically, the salts are present at concentrations from 10 mM to 500 mM.

The detergents may include Tween, SDS, Triton, CHAPS, deoxycholic acid, etc. The detergent may be present at concentrations from 0.01% to 10%. Typically, the detergents are present at concentrations from 0.1% to 1%.

The nucleic acid blocking agents may include, yeast tRNA, homopolymer DNA, denatured salmon sperm DNA, herring sperm DNA, total human DNA, COT1 DNA, etc. The blocking nucleic acids may be present at concentrations of 0.05 mg/mL to 100 mg/mL.

A great variation exists in the literature regarding traditional hybridization solutions. For example, a traditional hybridization solution may comprise 5× or 6×SSC, 0.01 M EDTA, 5× Dernhardt's solution, 0.5% SDS, and 100 mg/mL sheared, denatured salmon sperm DNA. Another traditional hybridization solution may comprise 50 mM HEPES, 0.5 M NaCl, and 0.2 mM EDTA. A typical hybridization solution for FISH on biological specimens for RNA detection may comprise, e.g., 2×SSC, 10% dextran sulfate, 2 mM vanadyl-ribonucleoside complex, 50% formamide, 0.02% RNAse-free BSA, and 1 mg/mL E. coli tRNA. A typical hybridization solution for FISH on biological specimens for DNA detection may comprise, e.g., 2×SSC, 10% dextran sulfate, 50% formamide, and e.g., 0.3 mg/mL salmon sperm DNA or 0.1 mg/mL COT1 DNA. Other typical hybridization solutions may comprise 40% formamide, 10% dextran sulfate, 30 mM NaCl, 5 mM phosphate buffer, Alu-PNA (blocking PNA) or COT-1 DNA, and in some cases 0.1 μg/μL total human DNA (THD).

The compositions of the invention may comprise a hybridization solution comprising any of the components of traditional hybridization solutions recited above in combination with at least one polar aprotic solvent. The traditional components may be present at the same concentrations as used in traditional hybridization solutions, or may be present at higher or lower concentrations, or may be omitted completely.

For example, if the compositions of the invention comprise salts such as NaCl and/or phosphate buffer, the salts may be present at concentrations of 0-1200 mM NaCl and/or 0-200 mM phosphate buffer. In some embodiments, the concentrations of salts may be, for example, 300 mM NaCl and 5 mM phosphate buffer, or 600 mM NaCl and 10 mM phosphate buffer.

If the compositions of the invention comprise accelerating agents such as dextran sulfate, glycol, or DMSO, the dextran sulfate may be present at concentrations of from 5% to 40%, the glycol may be present at concentrations of from 0.1% to 10%, and the DMSO may be from 0.1% to 10%. In some embodiments, the concentration of dextran sulfate may be 10% or 20% and the concentration of ethylene glycol, 1,3 propanediol, or glycerol may be 1% to 10%. In some embodiments, the concentration of DMSO may be 1%. In some embodiments, the aqueous composition does not comprise DMSO as an accelerating agent. In some embodiments, the aqueous composition does not comprise formamide as an accelerating agent, or comprises formamide with the proviso that the composition contains less than 10%, or less than 5%, or less than 2%, or less than 1%, or less than 0.5%, or less than 0.1%, or less than 0.05%, or less than 0.01%.

If the compositions of the invention comprise citric acid, the concentrations may range from 1 mM to 50 mM and the pH may range from 5.0 to 8.0. In some embodiments the concentration of citric acid may be 10 mM and the pH may be 6.2.

The compositions of the invention may comprise agents that reduce non-specific binding to, for example, the cell membrane, such as salmon sperm or small amounts of total human DNA or, for example, they may comprise blocking agents to block binding of, e.g., repeat sequences to the target such as larger amounts of total human DNA or repeat enriched DNA or specific blocking agents such as PNA or LNA fragments and sequences. These agents may be present at concentrations of from 0.01-100 µg/µL or 0.01-100 µM. For example, in some embodiments, these agents will be 0.1 µg/µL total human DNA, or 0.1 µg/µL non-human DNA, such as herring sperm, salmon sperm, or calf thymus DNA, or 5 µM blocking PNA.

One aspect of the invention is a composition or solution for use in hybridization. Compositions for use in the invention include an aqueous composition comprising a nucleic acid sequence and at least one polar aprotic solvent in an amount effective to denature double-stranded nucleotide sequences. An amount effective to denature double-stranded nucleotide sequences is an amount that enables hybridization. For example, one way to test for whether the amount of polar aprotic solvent is effective to enable hybridization is to determine whether the polar aprotic solvent, when used in the hybridization methods and compositions described herein, such as example 1, yield a detectable signal and/or an amplified nucleic acid product.

Non-limiting examples of effective amounts of polar aprotic solvents include, e.g., about 1% to about 95% (v/v). In some embodiments, the concentration of polar aprotic solvent is 5% to 60% (v/v). In other embodiments, the concentration of polar aprotic solvent is 10% to 60% (v/v). In still other embodiments, the concentration of polar aprotic solvent is 30% to 50% (v/v). Concentrations of 1% to 5%, 5% to 10%, 10%, 10% to 20%, 20% to 30%, 30% to 40%, 40% to 50%, or 50% to 60% (v/v) are also suitable. In some embodiments, the polar aprotic solvent will be present at a concentration of 0.1%, 0.25%, 0.5%, 1%, 2%, 3%, 4%, or 5% (v/v). In other embodiments, the polar aprotic solvent will be present at a concentration of 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% (v/v).

If the compositions of the invention are used in a hybridization assay, they may further comprise one or more nucleic acid probes. The probes may be directly or indirectly labeled with detectable compounds such as enzymes, chromophores, fluorochromes, and haptens. The DNA probes may be present at concentrations of 0.1 to 100 ng/µL. For example, in some embodiments, the probes may be present at concentrations of 1 to 10 ng/µL. The PNA probes may be present at concentrations of 0.5 to 5000 nM. For example, in some embodiments, the probes may be present at concentrations of 5 to 1000 nM.

In one embodiment, a composition of the invention comprises a mixture of 40% polar aprotic solvent (v/v) (e.g., ethylene carbonate, "EC"), 10% dextran sulfate, 300 mM NaCl, 5 mM phosphate buffer, and 1-10 ng/µL probe. Another exemplary composition of the present invention comprises a mixture of 15% EC, 20% dextran sulfate, 600 mM NaCl, 10 mM phosphate buffer, and 0.1 µg/µl total human DNA. Yet another exemplary composition comprises 15% EC, 20% dextran sulfate, 600 mM NaCl, 10 mM citric acid pH 6.2, and 0.1 µg/µL non-human DNA (e.g., herring sperm, salmon sperm, or calf thymus) OR 0.5% formamide OR 1% glycol (e.g., ethylene glycol, 1,3 propanediol, or glycerol).

(2) Polar Aprotic Solvent(s)

Different polar aprotic solvents may impart different properties on the compositions of the invention. For example, the choice of polar aprotic solvent may contribute to the stability of the composition, since certain polar aprotic solvents may degrade over time. For example, the polar aprotic solvent ethylene carbonate breaks down into ethylene glycol, which is a relatively stable molecule, and carbon dioxide, which can interact with water to form carbonic acid, altering the acidity of the compositions of the invention. Without being bound by theory, it is believed that the change in pH upon breakdown of ethylene carbonate makes the compositions of the invention less effective for hybridization. However, stability can be improved by reducing the pH of the composition, by adding citric acid as a buffer at pH 6.2 instead of the traditional phosphate buffer, which is typically used at about pH 7.4, and/or by adding ethylene glycol at concentrations, e.g., between 0.1% to 10%, or between 0.5% to 5%, such as, for example, 1%, 2%, 3%, etc. For example, with 10 mM citrate buffer, the compositions of the invention are stable at 2-8° C. for approximately 8 months. Stability can also be improved if the compositions are stored at low temperatures (e.g., −20° C.).

In addition, certain polar aprotic solvents may cause the compositions of the invention to separate into multi-phase systems under certain conditions. The conditions under which multi-phase systems are obtained may be different for different polar aprotic solvents. Generally, however, as the concentration of polar aprotic solvent increases, the number of phases increases. For example, compositions comprising low concentrations ethylene carbonate (i.e., less than 20%) may exist as one phase, while compositions comprising higher concentrations of ethylene carbonate may separate into two, or even three phases. For instance, compositions comprising 15% ethylene carbonate exist as a single phase at room temperature, while compositions comprising 40% ethylene carbonate consist of a viscous lower phase (approximately 25% of the total volume) and a less viscous upper phase (approximately 75% of the total volume) at room temperature.

On the other hand, some polar aprotic solvents may exist in two phases at room temperature even at low concentrations. For example, sulfolane, γ-butyrolactone, ethylene trithiocarbonate, glycol sulfite, and propylene carbonate exist as two phases at concentrations of 10, 15, 20, or 25% (20% dextran sulfate, 600 mM NaCl, 10 mM citrate buffer) at room temperature.

It may also be possible to alter the number of phases by adjusting the temperature of the compositions of the invention. Generally, as temperature increases, the number of phases decreases. For example, at 2-8° C., compositions comprising 40% ethylene carbonate may separate into a three-phase system.

It may also be possible to alter the number of phases by adjusting the concentration of dextran sulfate and/or salt in the composition. Generally speaking, lowering the dextran sulfate concentration (traditional concentration is 10%) and/or salt concentration may reduce the number of phases. However, depending on the particular polar aprotic solvent and its concentration in the composition, single phases may be produced even with higher concentrations of salt and dextran sulfate. For example, a composition comprising low amounts of EC (e.g., 15%, 10%, or 5%) can work well by increasing the dextran sulfate and salt concentrations, while still keeping a one phase system. In a particular embodiment, compositions comprising a HER2 gene DNA probe, a CEN7 PNA probe, 15% EC, 20% dextran sulfate, 600 mM NaCl, and 10 mM phosphate buffer are frozen at −20° C. In other embodiments, the compositions are liquid at −20° C.

Some polar aprotic solvents may produce stronger signals in one phase or another. For example, 40% glycol sulfite produces strong signals in the lower phase and no signals in the upper phase. Similarly, certain types of probes may produce stronger signals in one phase or another. For example, PNA probes tend to show stronger signals in the lower phase than the upper phase.

Accordingly, the multiphase systems of the invention may be used to conveniently examine different aspects of a sample. For example, a two-phase system could be used to separate samples labeled with PNA probes from samples labeled with DNA probes. Other uses include isolation of a specific phase exhibiting, e.g., certain hybridization advantages such that the isolated phase can be used as a single phase system. The probe and/or sample may be added prior to, or after isolation of a particular phase.

Hybridizations may be performed with a one-phase composition of the invention, with individual phases of the multiphase compositions of the invention, or with mixtures of any one or more of the phases in a multiphase composition of the invention. For example, in a one phase system, a volume of the sample may be extracted for use in the hybridization. In a mulitphase system, one may extract a volume of sample from the phase of interest (e.g., the upper, lower, or middle phase) to use in the hybridization. Alternatively, the phases in a multiphase system may be mixed prior to extracting a volume of the mixed sample for use in the hybridization. However, the multiphase system may yield strong and uneven local background staining depending on the composition. While, the addition of low amounts of formamide will reduce background in a one phase system, it has little effect on a multiphase system with high concentrations (e.g., 40%) of a polar aprotic solvent. In addition, as the concentration of formamide increases, higher concentrations of probe and/or longer hybridization times are required to maintain strong signal intensity.

(3) Optimization for Particular Applications

The compositions of the invention can be varied in order to optimize results for a particular application. For example, the concentration of polar aprotic solvent, salt, accelerating agent, blocking agent, and/or hydrogen ions (i.e. pH) may be varied in order to improve results for a particular application.

For example, the concentration of polar aprotic solvent may be varied in order to improve signal intensity and background staining. Generally, as the concentration of polar aprotic solvent increases, signal intensity increases and background staining decreases. For example, compositions comprising 15% EC tend to show stronger signals and less background than compositions comprising 5% EC. However, signal intensity may be improved for compositions having low concentrations of polar aprotic solvent (e.g., 0% to 20%) if the concentrations of salt and/or dextran sulfate are increased. For example, strong signals may be observed with 5% to 10% EC when the salt concentration is raised approximately 8 to 16 times traditional salt concentrations (i.e., approximately 1200 mM NaCl, 20 mM phosphate buffer). Likewise, as lower concentrations of polar aprotic solvent are used, higher concentrations of dextran sulfate are generally required to maintain good signal and background intensity.

Accordingly, the concentrations of salt and dextran sulfate may also be varied in order to improve signal intensity and background staining. Generally, as the concentrations of salt and dextran sulfate increase, the signal intensity increases and background decreases. For example, salt concentrations that are approximately two to four times traditional concentrations (i.e., 300 mM NaCl 5 mM phosphate buffer) produce strong signals and low background. Surprisingly, however, hybridization occurs using the compositions of the invention even in the complete absence of salt. Signal intensities can be improved under no-salt conditions by increasing the concentrations of accelerating agent and/or polar aprotic solvent.

Likewise, signal intensity increases as dextran sulfate concentration increases from 0% to 20%. However, good signals may even be observed at dextran sulfate concentrations of 0%. Signal intensity may be improved under low dextran sulfate conditions by increasing the polar aprotic solvent and/or salt concentrations.

In addition, the types probes used in the compositions of the invention may be varied to improve results. For example, in some aspects of the invention, combinations of DNA/DNA probes may show less background than combinations of DNA/PNA probes in the compositions of the invention or vice versa. On the other hand, PNA probes tend to show stronger signals than DNA probes under low salt and/or low polar aprotic solvent concentrations. In fact, PNA probes also show signals when no polar aprotic solvent is present, whereas DNA probes show weak or no signals without polar aprotic solvent.

D. Applications, Methods, and Uses (1) Analytical Samples

The methods and compositions of the invention may be used fully or partly in all types of hybridization applications in the fields of cytology, histology, or molecular biology.

According to one embodiment, the first or the second nucleic acid sequence in the methods of the invention is present in a biological sample. Examples of such samples include, e.g., tissue samples, cell preparations, cell fragment preparations, and isolated or enriched cell component preparations. The sample may originate from various tissues such as, e.g., breast, lung, colorectal, prostate, lung, head & neck, stomach, pancreas, esophagus, liver, and bladder, or other relevant tissues and neoplasia thereof, any cell suspension, blood sample, fine needle aspiration, ascites fluid, sputum, peritoneum wash, lung wash, urine, feces, cell scrape, cell smear, cytospin or cytoprep cells.

The sample may be isolated and processed using standard protocols. Cell fragment preparations may, e.g., be obtained by cell homogenizing, freeze-thaw treatment or cell lysing. The isolated sample may be treated in many different ways depending of the purpose of obtaining the sample and depending on the routine at the site. Often the sample is treated with various reagents to preserve the tissue for later sample analysis, alternatively the sample may be analyzed directly. Examples of widely used methods for preserving samples are formalin-fixed followed by paraffin-embedding and cryo-preservation.

For metaphase spreads, cell cultures are generally treated with colcemid, or another suitable spindle pole disrupting agent, to stop the cell cycle in metaphase. The cells are then fixed and spotted onto microscope slides, treated with formaldehyde, washed, and dehydrated in ethanol. Probes are then added and the samples are analyzed by any of the techniques discussed below.

Cytology involves the examination of individual cells and/or chromosome spreads from a biological sample. Cytological examination of a sample begins with obtaining a specimen of cells, which can typically be done by scraping, swabbing or brushing an area, as in the case of cervical specimens, or by collecting body fluids, such as those obtained from the chest cavity, bladder, or spinal column, or by fine needle aspiration or fine needle biopsy, as in the case of internal tumors. In a conventional manual cytological preparation, the sample is transferred to a liquid suspending material and the cells in the fluid are then transferred directly or by centrifugation-based processing steps onto a glass microscope slide for viewing. In a typical automated cytological preparation, a filter assembly is placed in the liquid suspension and the filter assembly both disperses the cells and captures the cells on the filter. The filter is then removed and placed in contact with a microscope slide. The cells are then fixed on the microscope slide before analysis by any of the techniques discussed below.

In a traditional hybridization experiment using a cytological sample, slides containing the specimen are immersed in a formaldehyde buffer, washed, and then dehydrated in ethanol. The probes are then added and the specimen is covered with a coverslip. The slide is incubated at a temperature sufficient to denature any nucleic acid in the specimen (e.g., 5 minutes at 82° C.) and then incubated at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

Histology involves the examination of cells in thin slices of tissue. To prepare a tissue sample for histological examination, pieces of the tissue are fixed in a suitable fixative, typically an aldehyde such as formaldehyde or glutaraldehyde, and then embedded in melted paraffin wax. The wax block containing the tissue sample is then cut on a microtome to yield thin slices of paraffin containing the tissue, typically from 2 to 10 microns thick. The specimen slice is then applied to a microscope slide, air dried, and heated to cause the specimen to adhere to the glass slide. Residual paraffin is then dissolved with a suitable solvent, typically xylene, toluene, or others. These so-called deparaffinizing solvents are then removed with a washing-dehydrating type reagent prior to analysis of the sample by any of the techniques discussed below. Alternatively, slices may be prepared from frozen specimens, fixed briefly in 10% formalin or other suitable fixative, and then infused with dehydrating reagent prior to analysis of the sample.

In a traditional hybridization experiment using a histological sample, formalin-fixed paraffin embedded tissue specimens are cut into sections of 2-6 μm and collected on slides. The paraffin is melted (e.g., 30-60 minutes at 60° C.) and then removed (deparaffinated) by washing with xylene (or a xylene substitute), e.g., 2×5 minutes. The samples are rehydrated, washed, and then pre-treated (e.g., 10 minutes at 95-100° C.). The slides are washed and then treated with pepsin or another suitable permeabilizer, e.g., 3-15 minutes at 37° C. The slides are washed (e.g., 2×3 minutes), dehydrated, and probe is applied. The specimens are covered with a coverslip and the slide is incubated at a temperature sufficient to denature any nucleic acid in the specimen (e.g. 5 minutes at 82° C.), followed by incubation at a temperature sufficient to allow hybridization (e.g., overnight at 45° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

(2) Hybridization Techniques

The compositions and methods of the present invention can be used fully or partly in all types of nucleic acid hybridization techniques known in the art for cytological and histological samples. Such techniques include, for example, in situ hybridization (ISH), fluorescent in situ hybridization (FISH; including multi-color FISH, Fiber-FISH, etc.), chromogenic in situ hybridization (CISH), silver in situ hybridization (SISH), comparative genome hybridization (CGH), chromosome paints, and arrays in situ.

Molecular probes that are suitable for use in the hybridizations of the invention are described, e.g., in U.S. Patent Publication No. 2005/0266459, which is incorporated herein by reference. In general, probes may be prepared by chemical synthesis or by amplifying a specific DNA sequence by cloning, inserting the DNA into a vector, and amplifying the vector an insert in appropriate host cells. Commonly used vectors include bacterial plasmids, cosmids, bacterial artificial chromosomes (BACs), PI diverted artificial chromosomes (PACs), or yeast artificial chromosomes (YACs). The amplified DNA is then extracted and purified for use as a probe. Methods for preparing and/or synthesizing probes are known in the art, e.g., as disclosed in PCT/US02/30573.

In general, the type of probe determines the type of feature one may detect in a hybridization assay. For example, total nuclear or genomic DNA probes can be used as a species-specific probe. Chromosome paints are collections of DNA sequences derived from a single chromosome type and can identify that specific chromosome type in metaphase and interphase nuclei, count the number of a certain chromosome, show translocations, or identify extra-chromosomal fragments of chromatin. Different chromosomal types also have unique repeated sequences that may be targeted for probe hybridization, to detect and count specific chromosomes. Large insert probes may be used to target unique single-copy sequences. With these large probes, the hybridization efficiency is inversely proportional to the probe size. Smaller probes can also be used to detect aberrations such as deletions, amplifications, inversions, duplications, and aneuploidy. For example, differently-colored locus-specific probes can be used to detect translocations via split-signal in situ hybridization.

In general, the ability to discriminate between closely related sequences is inversely proportional to the length of the hybridization probe because the difference in thermal stability decreases between wild type and mutant complexes as probe length increases. Probes of greater than 10 bp in length are generally required to obtain the sequence diversity necessary to correctly identify a unique organism or clinical condition of interest. On the other hand, sequence differences as subtle as a single base (point mutation) in very short oligomers (<10 base pairs) can be sufficient to enable the discrimination of the hybridization to complementary nucleic acid target sequences as compared with non-target sequences.

In one embodiment, at least one set of the in situ hybridization probes may comprise one or more PNA probes, as defined above and as described in U.S. Pat. No. 7,105,294, which is incorporated herein by reference. Methods for synthesizing PNA probes are described in PCT/US02/30573. Alternatively, or in addition, at least one set of the hybridization probes in any of the techniques discussed above may comprise one or more locked nucleic acid (LNA) probes, as described in WO 99/14226, which is incorporated herein by reference. Due to the additional bridging bond between the 2' and 4' carbons, the LNA backbone is pre-organized for hybridization. LNA/DNA and LNA/RNA interactions are stronger than the corresponding DNA/DNA and DNA/RNA interactions, as indicated by a higher melting temperature. Thus, the compositions and methods of the invention, which decrease the energy required for hybridization, are particularly useful for hybridizations with LNA probes.

In one embodiment, the probes may comprise a detectable label (a molecule that provides an analytically identifiable signal that allows the detection of the probe-target hybrid), as described in U.S. Patent Publication No. 2005/0266459, which is incorporated herein by reference. The detectable label may be directly attached to a probe, or indirectly attached to a probe, e.g., by using a linker. Any labeling method known to those in the art, including enzymatic and chemical processes, can be used for labeling probes used in the methods and compositions of the invention. In other embodiments, the probes are not labeled.

In general, in situ hybridization techniques such as CGH, FISH, CISH, and SISH, employ large, mainly unspecified, nucleic acid probes that hybridize with varying stringency to genes or gene fragments in the chromosomes of cells. Using large probes renders the in situ hybridization technique very sensitive. However, the successful use of large genomic probes in traditional hybridization assays depends on blocking the undesired background staining derived from, e.g., repetitive sequences that are present throughout the genome. Such blocking steps are time-consuming and expensive. As discussed below, the methods and compositions of the invention advantageously reduce and/or eliminate the need for such blocking steps. However, in one embodiment, repetitive sequences may be suppressed according to the methods known in the art, e.g., as disclosed in PCT/US02/30573.

Bound probes may be detected in cytological and histological samples either directly or indirectly with fluorochromes (e.g., FISH), organic chromogens (e.g., CISH), silver particles (e.g., SISH), or other metallic particles (e.g., gold-facilitated fluorescence in situ hybridization, GOLD-FISH). Thus, depending on the method of detection, populations of cells obtained from a sample to be tested may be visualized via fluorescence microscopy or conventional brightfield light microscopy.

Hybridization assays on cytological and histological samples are important tools for determining the number, size, and/or location of specific DNA sequences. For example, in CGH, whole genomes are stained and compared to normal reference genomes for the detection of regions with aberrant copy number. Typically, DNA from subject tissue and from normal control tissue is labeled with different colored probes. The pools of DNA are mixed and added to a metaphase spread of normal chromosomes (or to a microarray chip, for array- or matrix-CGH). The ratios of colors are then compared to identify regions with aberrant copy number.

FISH is typically used when multiple color imaging is required and/or when the protocol calls for quantification of signals. The technique generally entails preparing a cytological sample, labeling probes, denaturing target chromosomes and the probe, hybridizing the probe to the target sequence, and detecting the signal. Typically, the hybridization reaction fluorescently stains the targeted sequences so that their location, size, or number can be determined using fluorescence microscopy, flow cytometry, or other suitable instrumentation. DNA sequences ranging from whole genomes down to several kilobases can be studied using FISH. FISH may also be used on metaphase spreads and interphase nuclei.

FISH has been used successfully for mapping repetitive and single-copy DNA sequences on metaphase chromosomes, interphase nuclei, chromatin fibers, and naked DNA molecules, and for chromosome identification and karyotype analysis through the localization of large repeated families, typically the ribosomal DNAs and major tandem array families. One of the most important applications for FISH has been in detecting single-copy DNA sequences, in particular disease related genes in humans and other eukaryotic model species, and the detection of infections agents. FISH may be used to detect, e.g., chromosomal aneuploidy in prenatal diagnoses, hematological cancers, and solid tumors; gene abnormalities such as oncogene amplifications, gene deletions, or gene fusions; chromosomal structural abnormalities such as translocations, duplications, insertions, or inversions; contiguous gene syndromes such as microdeletion syndrome; the genetic effects of various therapies; viral nucleic acids in somatic cells and viral integration sites in chromosomes; etc. In multi-color FISH, each chromosome is stained with a separate color, enabling one to determine the normal chromosomes from which abnormal chromosomes are derived. Such techniques include multiplex FISH (m-FISH), spectral karyotyping (SKY), combined binary ration labeling (COBRA), color-changing karyotyping, cross-species color banding, high resolution multicolor banding, telomeric multiplex FISH (TM-FISH), split-signal FISH (ssFISH), and fusion-signal FISH.

CISH and SISH may be used for many of the same applications as FISH, and have the additional advantage of allowing for analysis of the underlying tissue morphology, for example in histopathology applications. If FISH is performed, the hybridization mixture may contain sets of distinct and balanced pairs of probes, as described in U.S. Pat. No. 6,730,474, which is incorporated herein by reference. For CISH, the hybridization mixture may contain at least one set of probes configured for detection with one or more conventional organic chromogens, and for SISH, the hybridization mixture may contain at least one set of probes configured for detection with silver particles, as described in Powell R D et al., "Metallographic in situ hybridization," Hum. Pathol., 38:1145-59 (2007).

The compositions of the invention may also be used fully or partly in all types of molecular biology techniques involving hybridization, including blotting and probing (e.g., Southern, northern, etc.), arrays, and amplification techniques including traditional PCR, RT-PCR, mutational PCR, asymmetric PCR, hot-start PCR, inverse PCR, multiplex PCR, nested PCR, quantitative PCR, and in situ PCR. In situ PCR is a polymerase chain reaction that takes place inside a cell on a slide, e.g., the cytology and histology samples described above. Typically, after adhering the sample to a microscope slide, the cells are re-hydrated and permeabilized, and then combined with an appropriate mixture of PCR reagents including polymerase, dNTPs, and primers. The PCR may be carried out in a dedicated instrument, such as the GeneAmp In situ PCR System 1000 (Perkin Elmer Biosystems, Foster City, Calif.), and the amplified product may be detected using labeled probes or by incorporating labeled dNTPs during the amplification. The compositions of the invention will improve the efficiency of traditional and in situ PCR analysis, e.g., by reducing the denaturation and hybridization temperatures and/or the time required in order to run the amplification cycles.

(3) Hybridization Conditions

The method of the present invention involves the use of polar aprotic solvents in hybridization of nucleic acid chains. The compositions of the present invention are particularly useful in said method.

Hybridization methods using the compositions of the invention may involve applying the compositions to a sample comprising a target nucleic acid sequence, most likely in a double stranded form. Usually, in order to secure access for the probe to hybridize with the target sequence, the sample and composition are heated to denature the target nucleic acids. During denaturation the polar aprotic solvent interacts with the sequence and facilitates the denaturation of the target and the re-annealing of the probe to target. The polar aprotic solvents specified in the present invention speed up this process considerably and reduce the harshness and toxicity of the hybridization conditions compared to formamide.

Hybridizations using the compositions of the invention may be performed using the same assay methodology as for hybridizations performed with traditional compositions. However, the compositions of the invention allow for shorter hybridization times. For example, the heat pre-treatment, digestion, denaturation, hybridization, washing, and mounting steps may use the same conditions in terms of volumes, temperatures, reagents and incubation times as for traditional compositions. A great variation exists in the traditional hybridization protocols known in the art. For example, some protocols specify a separate denaturation step of potential double stranded nucleotides without probe present, before the following hybridization step. The compositions of the invention may be used in any of traditional hybridization protocols known in the art.

Alternatively, assays using the compositions of the invention can be changed and optimized from traditional methodologies, for example, by decreasing the hybridization time, increasing or decreasing the denaturation and/or hybridization temperatures, and/or increasing or decreasing the hybridization volumes.

For example, in some embodiments, the compositions of the invention will produce strong signals when the denaturation temperature is from 60 to 100° C. and the hybridization temperature is from 20 to 60° C. In other embodiments, the compositions of the invention will produce strong signals when the denaturation temperature is from 60 to 70° C., 70 to 80° C., 80 to 90° C. or 90 to 100° C., and the hybridization temperature is from 20 to 30° C., 30 to 40° C., 40 to 50° C., or 50 to 60° C. In other embodiments, the compositions of the invention will produce strong signals when the denaturation temperature is 72, 82, or 92° C., and the hybridization temperature is 37, 40, 45, or 50° C.

In other embodiments, the compositions of the invention will produce strong signals when the denaturation time is from 0 to 10 minutes and the hybridization time is from 0 minutes to 24 hours. In other embodiments, the compositions of the invention will produce strong signals when the denaturation time is from 0 to 5 minutes and the hybridization time is from 0 minute to 8 hours. In other embodiments, the compositions of the invention will produce strong signals when the denaturation time is 0, 1, 2, 3, 4, or 5 minutes, and the hybridization time is 0 minutes, 5 minutes, 15 minutes, 30 minutes, 60 minutes, 180 minutes, or 240 minutes. It will be understood by those skilled in the art that in some cases, e.g., RNA detection, a denaturation step is not required.

Figure 2:
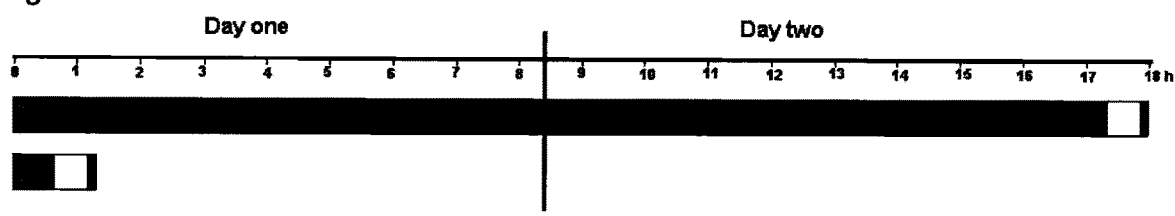
FIG. 2 depicts a typical time-course for single locus detection with primary labeled FISH probes on cytological specimens. The bars represent a hybridization performed using a traditional solution (top) and a typical time-course for a hybridization performed using a composition of the invention (bottom). The first bar on the left in each time-course represents the fixation step; the second bar represents the denaturation and hybridization step; the third bar represents the stringency wash step; and the fourth bar represents the mounting step.

Accordingly, hybridizations using the compositions of the invention may be performed in less than 8 hours. In other embodiments, the hybridization is performed in less than 6 hours. In still other embodiments, the hybridization is performed within 4 hours. In other embodiments, the hybridization is performed within 3 hours. In yet other embodiments, the hybridization is performed within 2 hours. In other embodiments, the hybridization is performed within 1 hour. In still other embodiments, the hybridization is performed within 30 minutes. In other embodiments, they hybridization can take place within 15 minutes. The hybridization can even take place within 10 minutes or in less than 5 minutes. FIGS. 1 and 2 illustrate a typical time-course for hybridizations performed on histological and cytological samples, respectively, using the compositions of the invention compared to hybridizations using a traditional compositions.

As hybridization time changes, the concentration of probe may also be varied in order to produce strong signals and/or reduce background. For example, as hybridization time decreases, the amount of probe may be increased in order to improve signal intensity. On the other hand, as hybridization time decreases, the amount of probe may be decreased in order to improve background staining.

The compositions of the invention surprisingly eliminate the need for a blocking step during hybridization by improving signal and background intensity by blocking the binding of, e.g., repetitive sequences to the target DNA. Thus, there is no need to use total human DNA, blocking-PNA, COT-1 DNA, or DNA from any other source as a blocking agent. However, background levels can be further reduced by adding agents that reduce non-specific binding, such as to the cell membrane, such as small amounts of total human DNA or non-human-origin DNA (e.g., salmon sperm DNA) to a hybridization reaction using the compositions of the invention.

The aqueous compositions of the invention furthermore provide for the possibility to considerably reduce the concentration of nucleic acid sequences included in the composition. Generally, the concentration of probes may be reduced from 2 to 8-fold compared to traditional concentrations. For example, if HER2 DNA probes and CEN17 PNA probes are used in the compositions of the invention, their concentrations may be reduced by ¼ and ½, respectively, compared to their concentrations in traditional hybridization compositions. This feature, along with the absence of any requirement for blocking DNA, such as blocking-PNA or COT1, allows for an increased probe volume in automated instrument systems compared to the traditional 10 µL volume used in traditional compositions systems, which reduces loss due to evaporation, as discussed in more detail below.

Reducing probe concentration also reduces background. However, reducing the probe concentration is inversely related to the hybridization time, i.e., the lower the concentration, the higher hybridization time required. Nevertheless, even when extremely low concentrations of probe are used with the aqueous compositions of the invention, the hybridization time is still shorter than with traditional compositions.

The compositions of the invention often allow for better signal-to-noise ratios than traditional hybridization compositions. For example, with certain probes, a one hour hybridization with the compositions of the invention will produce similar background and stronger signals than an overnight hybridization in a traditional compositions. Background is not seen when no probe is added.

Traditional assay methods may also be changed and optimized when using the compositions of the invention depending on whether the system is manual, semi-automated, or automated. For example, a semi- or an automated system will benefit from the short hybridization times obtained with the compositions of the invention. The short hybridization time may reduce the difficulties encountered when traditional compositions are used in such systems. For example, one problem with semi- and automated systems is that significant evaporation of the sample can occur during hybridization, since such systems require small sample volumes (e.g., 10-150 µL), elevated temperatures, and extended hybridization times (e.g., 14 hours). Thus, proportions of the components in traditional hybridization compositions are fairly invariable. However, since the compositions of the invention allow for faster hybridizations, evaporation is reduced, allowing for increased flexibility in the proportions of the components in hybridization compositions used in semi- and automated systems.

For example, two automated instruments have been used to perform hybridizations using the compositions of the invention. Compositions comprising 40% ethylene carbonate (v/v) have been used in the apparatus disclosed in PCT application DK2008/000430, and compositions comprising 15% ethylene carbonate (v/v) have been used in the HYBRIMASTER HS-300 (Aloka CO. LTD, Japan). When the compositions of the invention are used in the HYBRIMASTER HS-300, the instrument can perform rapid FISH hybridization with water in place of the traditional toxic formamide mix, thus improving safety and reducing evaporation. If water wetted strips are attached to the lid of the inner part of the Aloka instrument's reaction unit (hybridization chamber), e.g., as described in U.S. patent application Ser. No. 11/031,514, which is incorporated herein by reference, evaporation is reduced even further.

Another problem with automated imaging analysis is the number of images needed, the huge amount of storage place required, and the time required to take the images. The compositions of the invention address this problem by producing very strong signals compared to traditional compositions. Because of the very strong signals produced by the compositions of the invention, the imaging can be done at lower magnification than required for traditional compositions and can still be detected and analyzed, e.g., by algorithms. Since the focal plane becomes wider with lower magnification, the compositions of the invention reduce or eliminate the requirement to take serial sections of a sample. As a result, the overall imaging is much faster, since the compositions of the invention require fewer or no serial sections and each image covers much greater area. In addition, the overall time for analysis is faster, since the total image files are much smaller.

Thus, the compositions and methods of the invention solve many of the problems associated with traditional hybridization compositions and methods.

The disclosure may be understood more clearly with the aid of the non-limiting examples that follow, which constitute preferred embodiments of the compositions according to the disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements. The examples that follow illustrate the present invention and should not in any way be considered as limiting the invention.

EXAMPLES

Reference will now be made in detail to specific embodiments of the invention. While the invention will be described in conjunction with these embodiments, it will be understood that they are not intended to limit the invention to those embodiments. On the contrary, the invention is intended to cover alternatives, modifications, and equivalents, which may be included within the invention as defined by the appended claims.

The reagents used in the following examples are from Dako's Histology FISH Accessory Kit (K5599) and Cytology FISH Accessory Kit (K5499) (Dako Denmark A/S, Glostrup Denmark). The kits contain all the key reagents, except for probe, required to complete a FISH procedure for formalin-fixed, paraffin-embedded tissue section specimens. All samples were prepared according to the manufacturer's description. The Dako Hybridizer (S2450, Dako) was used for the digestion, denaturation, and hybridization steps.

Evaluation of FISH slides was performed within a week after hybridization using a Leica DM6000B fluorescence microscope, equipped with DAPI, FITC, Texas Red single filters and FITC/Texas Red double filter under 10×, 20×, 40×, and 100× oil objective.

Evaluation of CISH slides was performed using an Olympus BX51 light microscope, under 4×, 10×, 20×, 40×, and 60× objective.

In the Examples that follow, "dextran sulfate" refers to the sodium salt of dextran sulfate (D8906, Sigma) having a molecular weight $M_w > 500,000$. All concentrations of polar aprotic solvents are provided as v/v percentages. Phosphate buffer refers to a phosphate buffered solution containing $NaH_2PO_4$, $2H_2O$ (sodium phosphate dibasic dihydrate) and $Na_2HPO_4$, $H_2O$ (sodium phosphate monobasic monohydrate). Citrate buffer refers to a citrate buffered solution containing sodium citrate (Na$_3$C$_6$H$_5$O$_7$, 2H$_2$O; 1.06448, Merck) and citric acid monohydrate (C$_6$H$_8$O$_7$, H$_2$O; 1.00244, Merck).

General Histology FISH/CISH Procedure

Examples 1-20

The slides with cut formalin-fixed paraffin embedded (FFPE) multiple tissue array sections from humans (tonsils, mammacarcinoma, kidney and colon) were baked at 60° C. for 30-60 min, deparaffinated in xylene baths, rehydrated in ethanol baths and then transferred to Wash Buffer. The samples were then pre-treated in Pre-Treatment Solution at a minimum of 95° C. for 10 min and washed 2×3 min. The samples were then digested with Pepsin RTU at 37° C. for 3 min, washed 2×3 min, dehydrated in a series of ethanol evaporations, and air-dried. The samples were then incubated with 10 μL FISH probe as described under the individual experiments. The samples were then washed by Stringency Wash at 65° C. 10 min, then washed 2×3 min, then dehydrated in a series of ethanol evaporations, and air-dried. Finally, the slides were mounted with 15 μL Antifade Mounting Medium. When the staining was completed, observers trained to assess signal intensity, morphology, and background of the stained slides performed the scoring.

General Cytology FISH Procedure

Examples 21-22

Slides with metaphases preparation were fixed in 3.7% formaldehyde for 2 min, washed 2×5 min, dehydrated in a series of ethanol evaporations, and air-dried. The samples were then incubated with 10 μL FISH probe as described under the individual experiments. The samples were then washed by Stringency Wash at 65° C. 10 min, then washed 2×3 min, then dehydrated in a series of ethanol evaporations, and air-dried. Finally, the slides were mounted with 15 μL Antifade Mounting Medium. When the staining was completed, observers trained to assess signal intensity and background of the stained slides performed the scoring as described in the scoring for guidelines for tissue sections.

Scoring Guidelines of Tissue Sections

The signal intensities were evaluated on a 0-3 scale with 0 meaning no signal and 3 equating to a strong signal. The cell/tissue structures are evaluated on a 0-3 scale with 0 meaning no structure and no nuclei boundaries and 3 equating to intact structure and clear nuclei boundaries. Between 0 and 3 there are additional grades 0.5 apart from which the observer can assess signal intensity, tissue structure, and background.

The signal intensity is scored after a graded system on a 0-3 scale.
- 0 No signal is seen.
- 1 The signal intensity is weak.
- 2 The signal intensity is moderate.
- 3 The signal intensity is strong.

The scoring system allows the use of ½ grades.

The tissue and nuclear structure is scored after a graded system on a 0-3 scale.
- 0 The tissue structures and nuclear borders are completely destroyed.
- 1 The tissue structures and/or nuclear borders are poor. This grade includes situations where some areas have empty nuclei.
- 2 Tissue structures and/or nuclear borders are seen, but the nuclear borders are unclear. This grade includes situations where a few nuclei are empty.
- 3 Tissue structures and nuclear borders are intact and clear.

The scoring system allows the use of ½ grades.

The background is scored after a graded system on a 0-3 scale.
- 0 Little to no background is seen.
- 1 Some background.
- 2 Moderate background.
- 3 High Background.

The scoring system allows the use of ½ grades.

Example 1

This example compares the signal intensity and cell morphology from samples treated with the compositions of the invention or traditional hybridization solutions as a function of denaturation temperature.

FISH Probe composition I: 10% dextran sulfate, 300 mM NaCl, 5 mM phosphate buffer, 40% formamide (15515-026, Invitrogen), 5 μM blocking PNAs (see Kirsten Yang Nielsen et al., *PNA Suppression Method Combined with Fluorescence In Situ Hybridisation (FISH) Technique* inPRINS and PNA Technologies in Chromosomal Investigation, Chapter 10 (Franck Pellestor ed.) (Nova Science Publishers, Inc. 2006)), 10 ng/μL, Texas Red labeled CCND1 gene DNA probe (RP11-1143E20, size 192 kb).

FISH Probe composition II: 10% dextran sulfate, 300 mM NaCl, 5 mM phosphate buffer, 40% Ethylene carbonate (03519, Fluka), 5 μM blocking PNAs, 10 ng/μL, Texas Red labeled CCND1 gene DNA probe (RP11-1143E20, size 192 kb).

Phases of different viscosity, if present, were mixed before use. The FISH probes were denatured as indicated for 5 min and hybridized at 45° C. for 60 minutes.

Results:

|  | Signal | | Cell morphology | |
| --- | --- | --- | --- | --- |
| Denaturation | (I) | (II) | | |
| temperature | Formamide | EC | Formamide | EC |
| 72° C. | 0 | 2 | Good | Good |
| 82° C. | ½ | 3 | Good | Good |
| 92° C. | ½ | 3 | Not good | Not good |

Signals scored as "3" were clearly visible in a 20x objective.

Example 2

This example compares the signal intensity and background staining from samples treated with the compositions of the invention or traditional hybridization solutions as a function of hybridization time.

FISH Probe composition I: 10% dextran sulfate, 300 mM NaCl, 5 mM phosphate buffer, 40% formamide, 5 μM blocking PNAs, 10 ng/μL, Texas Red labeled CCND1 gene DNA probe.

FISH Probe composition II: 10% dextran sulfate, 300 mM NaCl, 5 mM phosphate buffer, 40% Ethylene carbonate, 5 μM blocking PNAs, 10 ng/μL Texas Red labeled CCND1 gene DNA probe.

Phases of different viscosity, if present, were mixed before use. The FISH probes were incubated at 82° C. for 5 min and then at 45° C. for 14 hours, 4 hours, 2 hours, 60 minutes, 30 minutes, 15 minutes, 0 minutes.
Results:

|  | Signal | | Background staining | |
| --- | --- | --- | --- | --- |
| Hybridization | (I) | (II) | | |
| time | Formamide | EC | Formamide | EC |
| 14 hours | 3 | 3 | +½ | +2 |
| 4 hours | 1 | 3 | +½ | +1 |
| 2 hours | ½ | 3 | +0 | +1 |
| 60 min. | ½ | 3 | +0 | +1 |
| 30 min. | 0 | 2½ | +0 | +1 |
| 15 min. | 0 | 2 | +0 | +1 |
| 0 min. | 0 | 1 | +0 | +½ |

Signals scored as "3" were clearly visible in a 20x objective.

Example 3

This example compares the signal intensity from samples treated with the compositions of the invention having different polar aprotic solvents or traditional hybridization solutions.

FISH Probe composition I: 10% dextran sulfate, 300 mM NaCl, 5 mM phosphate buffer, 40% formamide, 5 µM blocking PNAs, 10 ng/µL, Texas Red labeled CCND1 gene DNA probe.

FISH Probe composition II: 10% dextran sulfate, 300 mM NaCl, 5 mM phosphate buffer, 40% Ethylene carbonate (EC), 5 µM blocking PNAs, 10 ng/µL Texas Red labeled CCND1 gene DNA probe.

FISH Probe composition III: 10% dextran sulfate, 300 mM NaCl, 5 mM phosphate buffer, 40% Propylene carbonate (PC) (540013, Aldrich), 5 µM blocking PNAs, 10 ng/µL Texas Red labeled CCND1 gene DNA probe.

FISH Probe composition IV: 10% dextran sulfate, 300 mM NaCl, 5 mM phosphate buffer, 40% Sulfolane (SL) (T22209, Aldrich), 5 µM blocking PNAs, 10 ng/µL Texas Red labeled CCND1 gene DNA probe.

FISH Probe composition V: 10% dextran sulfate, 300 mM NaCl, 5 mM phosphate buffer, 40% Aceto nitrile (AN) (C02CIIX, Lab-Scan), 5 µM blocking PNAs, 10 ng/µL Texas Red labeled CCND1 gene DNA probe.

FISH Probe composition VI: 10% dextran sulfate, 300 mM NaCl, 5 mM phosphate buffer, 40% γ-butyrolactone (GBL) (B103608, Aldrich), 5 µM blocking PNAs, 7.5 ng/µL Texas Red labeled CCND1 gene DNA probe.

Phases of different viscosity, if present, were mixed before use. The FISH probes were incubated at 82° C. for 5 min and then at 45° C. for 60 minutes.
Results:

| | Signal | | | | | |
| --- | --- | --- | --- | --- | --- | --- |
| (I) Formamide | (II) EC | (III) PC | (IV) SL | (V) AN | (VI) GBL |
| ½ | 3 | 3 | 3 | 2 | 3 |

Signals scored as "3" were clearly visible in a 20x objective.

Example 4

This example compares the signal intensity from samples treated with the compositions of the invention having different concentrations of polar aprotic solvent.

FISH Probe Compositions: 10% dextran sulfate, 300 mM NaCl, 5 mM phosphate buffer, 10-60% Ethylene carbonate (as indicated), 5 µM blocking PNAs, 7.5 ng/µL Texas Red labeled IGK-constant DNA gene probe ((CTD-3050E15, RP11-1083E8; size 227 kb) and 7.5 ng/µL FITC labeled IGK-variable gene DNA probe (CTD-2575M21, RP11-122B6, RP11-316G9; size 350 and 429 kb).

Phases of different viscosity, if present, were mixed before use. The FISH probes were incubated at 82° C. for 5 min and then at 45° C. for 60 minutes.
Results:

| | | Ethylene carbonate (EC) | | | | |
| --- | --- | --- | --- | --- | --- | --- |
| | | 10% | 20% | 30% | 40% | 60% |
| Signal intensity | Texas Red | 1½ | 2 | 3 | 3 | 2 |
| | FITC | 1 | 1½ | 2 | 2½ | 2 |

Signals scored as "3" were clearly visible in a 20x objective.

Example 5

This example compares the signal intensity and background intensity from samples treated with the compositions with and without PNA blocking.

FISH Probe Compositions: 10% dextran sulfate, 300 mM NaCl, 5 mM phosphate buffer, 40% Ethylene carbonate, 7.5 ng/µL Texas Red labeled CCND1 gene DNA probe.

Phases of different viscosity, if present, were mixed before use. The FISH probes were incubated at 82° C. for 5 min and then at 45° C. for 60 minutes.
Results:

| | Ethylene carbonate (EC) | |
| --- | --- | --- |
| | PNA-blocking | Non-PNA blocking |
| Signal intensity | 3 | 3 |
| Background intensity | ½+ | ½+ |

Signals scored as "3" were clearly visible in a 20x objective.

Example 6

This example compares the signal intensity from samples treated with the compositions of the invention as a function of probe concentration and hybridization time.

FISH Probe Compositions: 10% dextran sulfate, 300 mM NaCl, 5 mM phosphate buffer, 40% Ethylene carbonate, and 10, 7.5, 5 or 2.5 ng/µL Texas Red labeled CCND1 gene DNA probe (as indicated).

Phases of different viscosity, if present, were mixed before use. The FISH probes were incubated at 82° C. for 5 min and then at 45° C. for 3 hours, 2 hours and 1 hours.
Results:

| | Signal Intensity | | | |
| --- | --- | --- | --- | --- |
| Hybridization time | (I) 10 ng/µL | (II) 7.5 ng/µL | (III) 5 ng/µL | (IV) 2.5 ng/µL |
| 3 hours | 3 | 3 | 3 | 3 |
| 2 hours | 3 | 3 | 3 | 1 |
| 1 hours | 3 | 3 | 3 | ½ |

Signals scored as "3" were clearly visible in a 20x objective.

Example 7

This example compares the signal intensity from samples treated with the compositions of the invention as a function of salt, phosphate, and buffer concentrations.

FISH Probe Compositions: 10% dextran sulfate, ([NaCl], [phosphate buffer], [TRIS buffer] as indicated in Results), 40% Ethylene carbonate, 7.5 ng/μL Texas Red labeled CCND1 gene DNA probe.

Phases of different viscosity, if present, were mixed before use. The FISH probes were incubated at 82° C. for 5 min and then at 45° C. for 60 minutes.

Results:

|  | [NaCl] | | |
| --- | --- | --- | --- |
|  | 300 mM | 100 mM | 0 mM |
| Signal intensity phosphate [0 mM] | 2 | 1 | ½ |
| Signal intensity phosphate [5 mM] | 3 | 2½ | ½ |
| Signal intensity phosphate [35 mM] | — | — | 3 |
| Signal intensity TRIS [40 mM] | — | — | 2 |

Signals scored as "3" were clearly visible in a 20x objective.

Example 8

This example compares the signal intensity from samples treated with the compositions of the invention as a function of dextran sulfate concentration.

FISH Probe Compositions: 0, 1, 2, 5, or 10% dextran sulfate (as indicated), 300 mM NaCl, 5 mM phosphate buffer, 40% Ethylene carbonate, 5 ng/μL Texas Red labeled SIL-TAL1 gene DNA probe (RP1-278013; size 67 kb) and 6 ng/μL FITC SIL-TAL1 (ICRFc112-112C1794, RP11-184J23, RP11-8J9, CTD-2007B18, 133B9; size 560 kb).

Phases of different viscosity, if present, were mixed before use. The FISH probes were incubated at 82° C. for 5 min and then at 45° C. for 60 minutes. No blocking.

Results:

|  | Signal Intensity | |
| --- | --- | --- |
| % Dextran Sulfate | Texas Red Probe | FITC Probe |
| 0% | 1 | 1 |
| 1% | 1 | 1 |
| 2% | 1½ | 1½ |
| 5% | 2 | 2½ |
| 10% | 2 | 2½ |

NOTE:
this experiment did not produce results scored as "3" because the SIL-TAL1 Texas Red labeled probe is only 67 kb and was from a non-optimized preparation.

Example 9

This example compares the signal intensity from samples treated with the compositions of the invention as a function of dextran sulfate, salt, phosphate, and polar aprotic solvent concentrations.

FISH Probe Composition Ia: 34% dextran sulfate, 0 mM NaCl, 0 mM phosphate buffer, 0% ethylene carbonate, 10 ng/μL Texas Red labeled HER2 gene DNA probe (size 218 kb) and 50 nM of FITC-labeled CEN-7 PNA probe.

FISH Probe Composition Ib: 34% dextran sulfate, 300 mM NaCl, 5 mM phosphate buffer, 0% ethylene carbonate, 10 ng/μL Texas Red labeled HER2 gene DNA probe (size 218 kb) and 50 nM of FITC-labeled CEN-7 PNA probe.

FISH Probe Composition Ic: 34% dextran sulfate, 600 mM NaCl, 10 mM phosphate buffer, 0% ethylene carbonate, 10 ng/μL Texas Red labeled HER2 gene DNA probe (size 218 kb) and 50 nM of FITC-labeled CEN-7 PNA probe.

FISH Probe Composition IIa: 32% dextran sulfate, 0 mM NaCl, 0 mM phosphate buffer, 5% ethylene carbonate, 10 ng/μL Texas Red labeled HER2 gene DNA probe (size 218 kb) and 50 nM of FITC-labeled CEN-7 PNA probe.

FISH Probe Composition IIb: 32% dextran sulfate, 300 mM NaCl, 5 mM phosphate buffer, 5% ethylene carbonate, 10 ng/μL Texas Red labeled HER2 gene DNA probe (size 218 kb) and 50 nM of FITC-labeled CEN-7 PNA probe.

FISH Probe Composition IIc: 32% dextran sulfate, 600 mM NaCl, 10 mM phosphate buffer, 5% ethylene carbonate, 10 ng/μL Texas Red labeled HER2 gene DNA probe (size 218 kb) and 50 nM of FITC-labeled CEN-7 PNA probe.

FISH Probe Composition IIIa: 30% dextran sulfate, 0 mM NaCl, 0 mM phosphate buffer, 10% ethylene carbonate, 10 ng/μL Texas Red labeled HER2 gene DNA probe (size 218 kb) and 50 nM of FITC-labeled CEN-7 PNA probe.

FISH Probe Composition IIIb: 30% dextran sulfate, 300 mM NaCl, 5 mM phosphate buffer, 10% ethylene carbonate, 10 ng/μL Texas Red labeled HER2 gene DNA probe (size 218 kb) and 50 nM of FITC-labeled CEN-7 PNA probe.

FISH Probe Composition IIIc: 30% dextran sulfate, 600 mM NaCl, 10 mM phosphate buffer, 10% ethylene carbonate, 10 ng/μL Texas Red labeled HER2 gene DNA probe (size 218 kb) and 50 nM of FITC-labeled CEN-7 PNA probe.

FISH Probe Composition IVa: 28% dextran sulfate, 0 mM NaCl, 0 mM phosphate buffer, 15% ethylene carbonate, 10 ng/μL Texas Red labeled HER2 gene DNA probe (size 218 kb) and 50 nM of FITC-labeled CEN-7 PNA probe.

FISH Probe Composition IVb: 28% dextran sulfate, 300 mM NaCl, 5 mM phosphate buffer, 15% ethylene carbonate, 10 ng/μL Texas Red labeled HER2 gene DNA probe (size 218 kb) and 50 nM of FITC-labeled CEN-7 PNA probe.

FISH Probe Composition IVc: 28% dextran sulfate, 600 mM NaCl, 10 mM phosphate buffer, 15% ethylene carbonate, 10 ng/μL Texas Red labeled HER2 gene DNA probe (size 218 kb) and 50 nM of FITC-labeled CEN-7 PNA probe.

FISH Probe Reference V: Standard sales vial of HER2 PharmDx probe mix (K5331, Dako) containing blocking PNA. Overnight hybridization for 20 hours.

All compositions were present as a single phase. The FISH probes were incubated at 82° C. for 5 min and then at 45° C. for 60 minutes with no blocking, except for FISH Probe Reference V, which had PNA blocking and was hybridized for 20 hours.

Results:

|  | Signal Strength | |
| --- | --- | --- |
|  | DNA Probes | PNA Probes |
| Composition Ia | 0 | ½ |
| Composition Ib | 0 | ½ |
| Composition Ic | ½ | 2½ |
| Composition IIa | ½ | 3 |
| Composition IIb | 1 | 2 |
| Composition IIc | ½ | 3 |
| Composition IIIa | 1 | 2½ |

-continued

|  | Signal Strength | |
| --- | --- | --- |
|  | DNA Probes | PNA Probes |
| Composition IIIb | 1½ | 2½ |
| Composition IIIc | 2 | 3 |
| Composition IVa | 2½-3 | 3 |
| Composition IVb | 3 | 3 |
| Composition IVc | 3 | 3 |
| Reference V | 2 | 2½ |

NOTE:
Composition IVa gave strong DNA signals with no salt. This is not possible with standard FISH compositions, where DNA binding is salt dependent.

Example 10

This example compares the signal intensity from samples treated with the compositions of the invention as a function of polar aprotic solvent and dextran sulfate concentration under high salt (4× normal) conditions.

FISH Probe Composition I: 0% ethylene carbonate, 29% dextran sulfate, 1200 mM NaCl, 20 mM phosphate buffer, 10 ng/μL Texas Red labeled HER2 gene DNA probe and 50 nM of FITC-labeled CEN-7 PNA probe. Composition was a single phase.

FISH Probe Composition II: 5% ethylene carbonate, 27% dextran sulfate, 1200 mM NaCl, 20 mM phosphate buffer, 10 ng/μL Texas Red labeled HER2 gene DNA probe and 50 nM of FITC-labeled CEN-7 PNA probe. Composition was a single phase.

FISH Probe Composition III: 10% ethylene carbonate, 25% dextran sulfate, 1200 mM NaCl, 20 mM phosphate buffer, 10 ng/μL Texas Red labeled HER2 gene DNA probe and 50 nM of FITC-labeled CEN-7 PNA probe. Composition was a single phase.

FISH Probe Composition IV (not tested): 20% ethylene carbonate, 21% dextran sulfate, 1200 mM NaCl, 20 mM phosphate buffer, 10 ng/μL Texas Red labeled HER2 gene DNA probe and 50 nM of FITC-labeled CEN-7 PNA probe. Composition had two phases.

Results:

|  | Signal Strength | |
| --- | --- | --- |
|  | DNA Probes | PNA Probes |
| Composition I | ½ | 3 |
| Composition II | 2 | 2½ |
| Composition III | 3 | 3 |
| Composition IV | — | — |

Note:
Composition II gave good DNA signals with only 5% EC and strong DNA signals with 10% EC.

Example 11

This example compares the signal intensity and background from samples treated with different phases of the compositions of the invention.

FISH Probe Composition: 10% dextran sulfate, 300 mM NaCl, 5 mM phosphate buffer, 40% Ethylene carbonate, 8 ng/μL Texas Red labeled HER2 gene DNA probe and 600 nM FITC-labeled CEN-17 PNA probe. The FISH probes were incubated at 82° C. for 5 min and then at 45° C. for 60 minutes. No blocking.

Results:

|  | Signal Intensity | | |
| --- | --- | --- | --- |
|  | DNA Probe | PNA Probe | Background |
| Upper Phase | 3 | 1½ | +2 |
| Lower Phase | 3 | 2½ | +1 |
| Mix of Upper and Lower Phases | 2½ | 3 | +½ |

NOTE:
the upper phase had more background than the lower phase in these experiments.

Example 12

This example is similar to the previous example, but uses a different DNA probe and GBL instead of EC.

FISH Probe Composition: 10% dextran sulfate, 300 mM NaCl, 5 mM phosphate buffer, 40% GBL, 10 ng/μL Texas Red labeled CCND1 gene DNA probe and 600 nM FITC-labeled CEN-17 PNA probe.

The FISH probes were incubated at 82° C. for 5 min and then at 45° C. for 60 minutes. No blocking.

Results:

|  | Signal Strength | | |
| --- | --- | --- | --- |
|  | DNA Probe | PNA Probe | Background |
| Top Phase | 3 | 0-½ | +1½ |
| Bottom Phase | 2 | ½ | +3 |
| Mixed Phases | 2½ | ½ | +2½ |

Example 13

This example examines the number of phases in the compositions of the invention as a function of polar aprotic solvent and dextran sulfate concentration.

FISH Probe Compositions: 10 or 20% dextran sulfate; 300 mM NaCl; 5 mM phosphate buffer; 0, 5, 10, 15, 20, 25, 30% EC; 10 ng/μL probe.

Results:

| % EC | Number of Phases 10% Dextran | Number of Phases 20% Dextran |
| --- | --- | --- |
| 0 | 1 | 1 |
| 5 | 1 | 1 |
| 10 | 1 | 1 |
| 15 | 1 | 1 |
| 20 | 2 | 2 |
| 25 | 2 | 2 |
| 30 | 2 | 2 |

NOTE:
15% EC, 20% dextran sulfate produces the nicest high signal intensities of the above one phase solution. Two phases 20% EC has even higher signal intensities than 15%. (Data not shown).

Example 14

This example compares the signal intensity and background from samples treated with different compositions of the invention as a function of probe concentration and hybridization time.

FISH Probe Composition I: 10 ng/μL HER2 TxRed labeled DNA probe (standard concentration) and standard concentration of CEN7 FITC labeled PNA probe (50 nM); 15% EC; 20% dextran sulfate; 600 mM NaCl; 10 mM phosphate buffer.

FISH Probe Composition II: 5 ng/μL HER2 TxRed labeled DNA probe (½ of standard concentration) and standard concentration (50 nM) of FITC labeled CEN7 PNA probes; 15% EC; 20% dextran sulfate; 600 mM NaCl; 10 mM phosphate buffer.

FISH Probe Composition III: 2.5 ng/μL HER2 TxRed labeled DNA probe (¼ of standard concentration) and ½ of the standard concentration (25 nM) of CEN7 PNA probes; 15% EC; 20% dextran sulfate; 600 mM NaCl; 10 mM phosphate buffer.

Compositions I-III existed as a single phase. The FISH probes were incubated at 82° C. for 5 min and then at 45° C. for 3 hours, 2 hours and 1 hours.

Results:

| Hybrid- | Signal Intensity | | | | | | | | |
|---|---|---|---|---|---|---|---|---|---|
| ization | I | | | II | | | III | | |
| time | DNA | PNA | B.G. | DNA | PNA | E.G. | DNA | PNA | B.G. |
| 3 hours | 3 | 3 | +3 | 3 | 3 | +2.5 | 3 | 3 | +1.5 |
| 2 hours | 2.5 | 2.5 | +3 | 3 | 3 | +3 | 3 | 3 | +1.5 |
| 1 hours | 2.5 | 2.5 | +3 | 3 | 3 | +1.5 | 2.5 | 3 | +1 |

Signals scored as "3" were clearly visible in a 20x objective. B.G.: Back ground.

Example 15

This example compares the signal intensity and background from samples treated with the compositions of the invention as a function of blocking agent.

FISH Probe Compositions: 15% EC; 20% dextran sulfate; 600 mM NaCl; 10 mM phosphate buffer; 2.5 ng/μL HER2 TxRed labeled DNA probe (¼ of standard concentration) and ½ of the standard concentration (300 nM) FITC labeled CEN17 PNA probe. Samples were blocked with: (a) nothing; (b) 0.1 μg/μL COT1 (15279-011, Invitrogen); (c) 0.3 μg/μL COT1; or (d) 0.1 μg/μL total human DNA before hybridization using the compositions of the invention.

All samples were present as a single phase. The FISH probes were incubated at 82° C. for 5 min and then at 45° C. for 60 minutes.

Results:

| | | Signal Intensity | |
|---|---|---|---|
| Blocking Agent | Background | DNA | PNA |
| Nothing | +1-1.5 | 3 | 2.5 |
| 0.1 μg/μL COT1 | +1 | 3 | 2.5 |
| 0.3 μg/μL COT1 | +1.5 | 3 | 2.5 |
| 0.1 μg/μL total human DNA | +½ | 3 | 2.5 |

NOTE:
Background levels without blocking are significantly lower than what is normally observed by standard FISH with no blocking. In contrast, if a standard FISH composition does not contain a blocking agent, signals normally cannot be read.

Example 16

This experiment compares different ways of removing background staining using the compositions of the invention.

All compositions contained 15% EC, 20% dextran sulfate, 600 mM NaCl, 10 mM phosphate buffer, 2.5 ng/μL HER2 DNA probes (¼ of standard concentration), 300 nM CEN17 PNA probe (½ of standard concentration), and one of the following background-reducing agents:

A) 5 μM blocking-PNA (see Kirsten yang Nielsen et al., *PNA Suppression Method Combined with Fluorescence In Situ Hybridisation (FISH) Technique* inPRINS and PNA Technologies in Chromosomal Investigation, Chapter 10 (Franck Pellestor ed.) (Nova Science Publishers, Inc. 2006))
B) 0.1 μg/μL COT-1 DNA
C) 0.1 μg/mL total human DNA (THD) (sonicated unlabelled THD)
D) 0.1 μg/μL sheared salmon sperm DNA (AM9680, Ambion)
E) 0.1 μg/μL calf thymus DNA (D8661, Sigma)
F) 0.1 μg/μL herring sperm DNA (D7290, Sigma)
G) 0.5% formamide
H) 2% formamide
I) 1% ethylene glycol (1.09621, Merck)
J) 1% glycerol (1.04095, Merck)
K) 1% 1,3-Propanediol (533734, Aldrich)
L) 1% H$_2$O (control)

All samples were present as a single phase. The probes were incubated at 82° C. for 5 minutes and then at 45° C. on FFPE tissue sections for 60 and 120 minutes.

Results:

| | | | Signal Intensity | |
|---|---|---|---|---|
| Background blocking | Hybridization/mm | Background | DNA | PNA |
| Blocking-PNA | 60 | +1 | 3 | 2.5 |
| Blocking-PNA | 120 | +1-1½ | 3 | 2.5 |
| COT-1 | 60 | +½ | 3 | 2.5 |
| COT-1 | 120 | +0-½ | 3 | 2.5 |
| THD | 60 | +0 | 3 | 3 |
| THD | 120 | +½ | 3 | 2.5 |
| Salmon DNA sperm | 60 | +0 | 3 | 3 |
| Salmon DNA sperm | 120 | +0 | 3 | 3 |
| Calf Thymus DNA | 60 | +0 | 2.5 | 3 |
| Calf Thymus DNA | 120 | +½ | 3 | 2.5 |
| Hearing sperm DNA | 60 | +0 | 3 | 3 |
| Hearing sperm DNA | 120 | +½ | 2.5 | 3 |
| 0.5% formamide | 60 | +0 | 2.5 | 3 |
| 0.5% formamide | 120 | +0 | 3 | 3 |
| 2% formamide | 60 | +½ | 2.5 | 3 |
| 2% formamide | 120 | +½ | 3 | 3 |
| 1% Ethylene Glycol | 60 | +½ | 2.5 | 3 |
| 1% Ethylene Glycol | 120 | +1½ | 3 | 2.5 |
| 1% Glycerol | 60 | +½ | 0.5 | 3 |
| 1% Glycerol | 120 | +1 | 3 | 2.5 |
| 1% 1,3-Propanediol | 60 | +0 | 3 | 3 |
| 1% 1,3-Propanediol | 120 | +1 | 3 | 2.5 |
| Nothing | 60 | +1 | 2.5 | 2.5 |
| Nothing | 120 | +1½ | 3 | 2.5 |

NOTE:
all background reducing reagents, except for blocking-PNA, showed an effect in background reduction. Thus, specific blocking against repetitive DNA sequences is not required.

Example 17

This experiment compares the signal intensity from the upper and lower phases using two different polar aprotic solvents.

FISH Probe Composition I: 10% dextran sulfate, 300 mM NaCl, 5 mM phosphate buffer, 40% ethylene trithiocarbonate (ET) (E27750, Aldrich), 5 μM blocking PNAs, 10 ng/μL Texas Red labeled CCND1 gene DNA probe.

FISH Probe Composition II: 10% dextran sulfate, 300 mM NaCl, 5 mM phosphate buffer, 40% glycol sulfite (GS) (G7208, Aldrich), 5 μM blocking PNAs, 10 ng/μL Texas Red labeled CCND1 gene DNA probe.

The FISH probes were incubated at 82° C. for 5 min and then at 45° C. for 60 minutes.

Results:

|  | Signal Intensity | |
|---|---|---|
|  | I (ET) | II (GS) |
| Upper Phase | 1½ | 0 |
| Lower Phase | 0 | 3 |
| Mix of Upper and Lower Phases | 2½ | 3 |

Example 18

This experiment examines the ability of various polar aprotic solvents to form a one-phase system.

All compositions contained: 20% dextran sulfate, 600 mM NaCl, 10 mM phosphate buffer, and either 10, 15, 20, or 25% of one of the following polar aprotic solvents:
Sulfolane
γ-Butyrolactone
Ethylene trithiocarbonate
Glycol sulfite
Propylene carbonate Results: all of the polar aprotic solvents at all of the concentrations examined produced at least a two-phase system in the compositions used. However, this does not exclude that these compounds can produce a one-phase system under other composition conditions.

Example 19

This experiment examines the use of the compositions of the invention in chromogenic in situ hybridization (CISH) analysis on multi FFPE tissue sections.

FISH Probe Composition I: 4.5 ng/μL TCRAD FITC labelled gene DNA probe (¼ of standard concentration) (RP11-654A2, RP11-246A2, CTP-2355L21, RP11-158G6, RP11-780M2, RP11-481C14; size 1018 kb); 15% EC; 20% dextran sulfate; 600 mM NaCl; 10 mM citrate buffer, pH 6.0.

FISH Probe Composition II: 4.5 ng/μL TCRAD FITC labelled gene DNA probe (¼ of standard concentration) (size 1018 kb); 15% EC; 20% dextran sulfate; 600 mM NaCl; 10 mM citrate buffer, pH 6.0; 0.1 ug/uL sheared salmon DNA sperm.

FISH Probe Composition III: 300 nM of each individual FITC labelled PNA CEN17 probe (½ of standard concentration); 15% EC; 20% dextran sulfate; 600 mM NaCl; 10 mM citrate buffer, pH 6.0.

All samples were analyzed using the Dako DuoCISH protocol (SK108) and compositions for split probes with the exception that the stringency wash was conducted for 20 minutes instead of 10 minutes, and without using the DuoCISH red chromogen step.

Results:

|  | Signal Strength | |
|---|---|---|
| Composition | FITC DNA | FITC PNA |
| I | 3 | — |
| II | 3 | — |
| III | — | 3 |

Note:
The signal intensities were very strong. Due to the high levels of background, it was not possible to discriminate if addition of salmon sperm DNA in Composition II reduced the background. Signals were clearly visible using a 10x objective in e.g. tonsils, which in general had less background. If tissues possessed high background, the signals were clearly visible using a 20x objective.

Example 20

This example compares the signal intensity and background from FFPE tissue sections treated with the compositions of the invention with two DNA probes.

FISH Probe Composition I: 9 ng/μL IGH FITC labelled gene DNA probe (RP11-151B17, RP11-112H5, RP11-101G24, RP11-12F16, RP11-47P23, CTP-3087C18; size 612 kb); 6.4 ng/μL MYC Tx Red labeled DNA probe (CTD-2106F24, CTD-2151C21, CTD-2267H22; size 418 kb); 15% EC; 20% dextran sulfate; 600 mM NaCl; 10 mM citrate buffer, pH 6.0.

FISH Probe Composition II: 9 ng/μL IGH FITC labelled gene DNA probe; 6.4 ng MYC TxRed labeled DNA probe; 15% EC, 20% dextran sulfate; 600 mM NaCl; 10 mM citrate buffer, pH 6.0; 0.1 ug/uL sheared salmon sperm DNA.

|  | Signal Strength | | |
|---|---|---|---|
| Salmon DNA | FITC probe | Texas Red probe | Background |
| − | 2½ | 2½ | +2.5 |
| + | 3 | 3 | +1.5 |

NOTE:
the high background was probably due to the fact that standard probe concentrations were used.

Example 21

This experiment examines the use of the compositions of the invention on cytological samples.

FISH Probe Composition: 15% EC; 20% dextran sulfate; 600 mM NaCl; 10 mM phosphate buffer; 5 ng/μL HER2 TxRed labeled DNA probe (½ of standard concentration) and ½ of the standard concentration of CENT (25 nM).

The FISH probes were incubated on metaphase chromosome spreads at 82° C. for 5 minutes, then at 45° C. for 30 minutes, all without blocking.

Results:

| Signal Strength | | |
|---|---|---|
| DNA Probe | PNA Probe | Background |
| 3 | 3 | +1 |

No chromosome banding (R-banding pattern) was observed with the compositions of the invention, in contrast with traditional ISH solutions, which typically show R-banding. A low homogenously red background staining of the interphase nuclei and metaphase chromosomes was observed.

Example 22

This example compares the signal intensity and background from DNA probes on cytology samples, metaphase spreads, with and without blocking.

FISH Probe Composition I: 6 ng/μL TCRAD Texas Red labelled gene DNA probe (standard concentration) (CTP-31666K20, CTP-2373N7; size 301 kb) and 4.5 ng/μL FITC labelled gene DNA probe (¼ of standard concentration); 15% EC, 20% dextran sulfate; 600 mM NaCl; 10 mM citrate buffer, pH 6.0.

FISH Probe Composition 6 ng/μL TCRAD Texas Red labelled gene DNA probe (standard concentration) (size 301 kb) and 4.5 ng/μL FITC labelled gene DNA probe (¼ of standard concentration); 15% EC, 20% dextran sulfate; 600 mM NaCl; 10 mM citrate buffer, pH 6.0; 0.1 ug/uL sheared salmon sperm DNA.

The FISH probes were incubated on metaphase spreads at 82° C. for 5 min, then at 45° C. for 60 min.

Results:

| | | Signal Intensity | |
|---|---|---|---|
| Blocking Agent | Background | Tx Red | FITC |
| Nothing | +0 | 3 | 3 |
| 0.1 μg/μL Salmon DNA | +0 | 3 | 3 |

Again, no chromosome banding (R-banding pattern) was observed with the compositions of the invention. In addition, no background staining of the interphase nuclei or the metaphase chromosomes were observed.

FURTHER EMBODIMENTS

Embodiment 1

A hybridization composition comprising at least one nucleic acid sequence, at least one polar aprotic solvent in an amount effective to denature double-stranded nucleotide sequences, and a hybridization solution, wherein the polar aprotic solvent is not dimethyl sulfoxide (DMSO).

Embodiment 2

The hybridization composition according to embodiment 1, wherein the concentration of polar aprotic solvent is about 1% to 95% (v/v)

Embodiment 3

The hybridization composition according to embodiment 1 or 2, wherein the concentration of polar aprotic solvent is 5% to 10% (v/v).

Embodiment 4

The hybridization composition according to embodiment 1 or 2, wherein the concentration of polar aprotic solvent is 10% to 20% (v/v).

Embodiment 5

The hybridization composition according to embodiment 1 or 2, wherein the concentration of polar aprotic solvent is 20% to 30% (v/v).

Embodiment 6

The hybridization composition according to any one of embodiments 1 to 5, wherein the polar aprotic solvent is non-toxic.

Embodiment 7

The hybridization composition according to any one of embodiments 1 to 6, with the proviso that the composition does not contain formamide.

Embodiment 8

The hybridization composition according to embodiment 6, with the proviso that the composition contains less than 10% formamide.

Embodiment 9

The hybridization composition according to embodiment 8, with the proviso that the composition contains less than 2% formamide.

Embodiment 10

The hybridization composition according to embodiment 9, with the proviso that the composition contains less than 1% formamide.

Embodiment 11

The hybridization composition according to any of embodiments 1 to 10, wherein the polar aprotic solvent has lactone, sulfone, nitrile, sulfite, and/or carbonate functionality.

Embodiment 12

The hybridization composition according to any one of embodiments 1 to 11, wherein the polar aprotic solvent has a dispersion solubility parameter between 17.7 to 22.0 $MPa^{1/2}$, a polar solubility parameter between 13 to 23 $MPa^{1/2}$, and a hydrogen bonding solubility parameter between 3 to 13 $MPa^{1/2}$.

Embodiment 13

The hybridization composition according to any one of embodiments 1 to 12, wherein the polar aprotic solvent has a cyclic base structure.

Embodiment 14

The hybridization composition according to any one of embodiments 1 to 13, wherein the polar aprotic solvent is selected from the group consisting of:

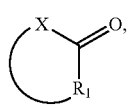

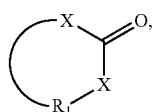

-continued

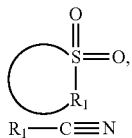

where X is O and R1 is alkyldiyl, and

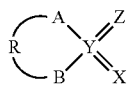

where X is optional and if present, is chosen from O or S,
where Z is optional and if present, is chosen from O or S,
where A and B independently are O or N or S or part of the alkyldiyl or a primary amine,
where R is alkyldiyl, and
where Y is O or S or C.

Embodiment 15

The hybridization composition according to any one of embodiments 1 to 14, wherein the polar aprotic solvent is selected from the group consisting of: acetanilide, acetonitrile, N-acetyl pyrrolidone, 4-amino pyridine, benzamide, benzimidazole, 1,2,3-benzotriazole, butadienedioxide, 2,3-butylene carbonate, γ-butyrolactone, caprolactone (epsilon), chloro maleic anhydride, 2-chlorocyclohexanone, chloroethylene carbonate, chloronitromethane, citraconic anhydride, crotonlactone, 5-cyano-2-thiouracil, cyclopropylnitrile, dimethyl sulfate, dimethyl sulfone, 1,3-dimethyl-5-tetrazole, 1,5-dimethyl tetrazole, 1,2-dinitrobenzene, 2,4-dinitrotoluene, dipheynyl sulfone, 1,2-dinitrobenzene, 2,4-dinitrotoluene, dipheynyl sulfone, epsilon-caprolactam, ethanesulfonylchloride, ethyl ethyl phosphinate, N-ethyl tetrazole, ethylene carbonate, ethylene trithiocarbonate, ethylene glycol sulfate, glycol sulfite, furfural, 2-furonitrile, 2-imidazole, isatin, isoxazole, malononitrile, 4-methoxy benzonitrile, 1-methoxy-2-nitrobenzene, methyl alpha bromo tetronate, 1-methyl imidazole, N-methyl imidazole, 3-methyl isoxazole, N-methyl morpholine-N-oxide, methyl phenyl sulfone, N-methyl pyrrolidinone, methyl sulfolane, methyl-4-toluenesulfonate, 3-nitroaniline, nitrobenzimidazole, 2-nitrofuran, 1-nitroso-2-pyrrolidinone, 2-nitrothiophene, 2-oxazolidinone, 9,10-phenanthrenequinone, N-phenyl sydnone, phthalic anhydride, picolinonitrile (2-cyanopyridine), 1,3-propane sultone, β-propiolactone, propylene carbonate, 4H-pyran-4-thione, 4H-pyran-4-one (γ-pyrone), pyridazine, 2-pyrrolidone, saccharin, succinonitrile, sulfanilamide, sulfolane, 2,2,6,6-tetrachlorocyclohexanone, tetrahydrothiapyran oxide, tetramethylene sulfone (sulfolane), thiazole, 2-thiouracil, 3,3,3-trichloro propene, 1,1,2-trichloro propene, 1,2,3-trichloro propene, trimethylene sulfide-dioxide, and trimethylene sulfite.

Embodiment 16

The hybridization composition according to any one of embodiments 1 to 14, wherein the polar aprotic solvent is selected from the group consisting of

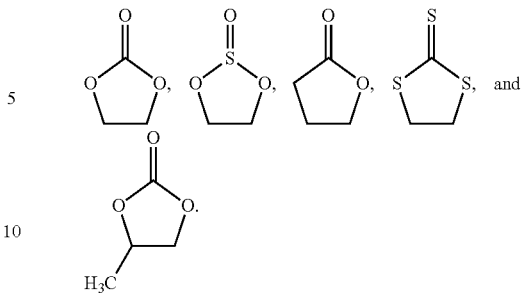

Embodiment 17

The hybridization composition according to any one of embodiments 1 to 14, wherein the polar aprotic solvent is:

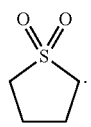

Embodiment 18

The hybridization composition according to any one of embodiments 1 to 17, further comprising at least one additional component selected from the group consisting of: buffering agents, salts, accelerating agents, chelating agents, detergents, and blocking agents.

Embodiment 19

The hybridization composition according to embodiment 18, wherein the accelerating agent is dextran sulfate and the salts are NaCl and/or phosphate buffer.

Embodiment 20

The hybridization composition according to embodiment 19, wherein the dextran sulfate is present at a concentration of 5% to 40%, the NaCl is present at a concentration of 0 mM to 1200 mM, and/or the phosphate buffer is present at a concentration of 0 mM to 50 mM.

Embodiment 21

The hybridization composition according to embodiment 20, wherein the dextran sulfate is present at a concentration of 10% to 30%, the NaCl is present at a concentration of 300 mM to 600 mM, and/or the phosphate buffer is present at a concentration of 5 mM to 20 mM.

Embodiment 22

The hybridization composition according to embodiment 18, wherein the accelerating agent is selected from the group consisting of formamide, glycerol, propylene glycol, 1,2-propanediol, diethylene glycol, ethylene glycol, glycol, and 1,3 propanediol, and the buffering agent is citric acid buffer.

Embodiment 23

The hybridization composition according to embodiment 22, wherein the formamide is present at a concentration of 0.1-5%, the glycerol, propylene glycol, 1,2-propanediol, diethylene glycol, ethylene glycol, glycol, and 1,3 propanediol are present at a concentration of 0.1% to 10%, and the citric acid buffer is present at a concentration of 1 mM to 50 mM.

Embodiment 24

The hybridization composition according to embodiment 18, wherein the blocking agent is selected from the group consisting of: total human DNA, herring sperm DNA, salmon sperm DNA, and calf thymus DNA.

Embodiment 25

The hybridization composition according to embodiment 24, wherein the total human DNA, herring sperm DNA, salmon sperm DNA, and calf thymus DNA are present at a concentration of 0.01 to 10 µg/µL.

Embodiment 26

The hybridization composition according to any one of embodiments 1-25, comprising 40% of at least one polar aprotic solvent, 10% dextran sulfate, 300 mM NaCl, and 5 mM phosphate buffer.

Embodiment 27

The hybridization composition according to any one of embodiments 1-25, comprising 15% of at least one polar aprotic solvent, 20% dextran sulfate, 600 mM NaCl, 10 mM phosphate buffer, and 0.1 µg/µl total human DNA.

Embodiment 28

The hybridization composition according to any one of embodiments 1-25, comprising 15% of at least one polar aprotic solvent, 20% dextran sulfate, 600 mM NaCl, 10 mM citric acid buffer pH 6.2, and 0.1 µg/µL herring sperm DNA, or salmon sperm DNA, or calf thymus DNA, or 0.5% formamide, or 1% ethylene glycol, or 1% 1,3 propanediol.

Embodiment 29

The hybridization composition according to any one of embodiments 1-28, comprising more than one phase at room temperature.

Embodiment 30

The hybridization composition according to embodiment 29, comprising two phases at room temperature.

Embodiment 31

The hybridization composition according to embodiment 29, comprising three phases at room temperature.

Embodiment 32

A method of hybridizing nucleic acid sequences comprising:
  providing a first nucleic acid sequence,
  providing a second nucleic acid sequence,
  providing a hybridization composition comprising at least one polar aprotic solvent in an amount effective to denature double-stranded nucleotide sequences, and
  combining the first and the second nucleic acid sequence and the hybridization composition for at least a time period sufficient to hybridize the first and second nucleic acid sequences,
wherein the polar aprotic solvent is not dimethyl sulfoxide (DMSO).

Embodiment 33

A method of hybridizing nucleic acid sequences comprising:
  providing a first nucleic acid sequence in an in situ biological sample, and
  applying a hybridization composition comprising a second nucleic acid sequence and at least one polar aprotic solvent in an amount effective to denature double-stranded nucleotide sequences to said first nucleic acid sequence for at least a time period sufficient to hybridize the first and second nucleic acid sequences,
wherein the polar aprotic solvent is not dimethyl sulfoxide (DMSO).

Embodiment 34

A method of hybridizing nucleic acid sequences comprising:
  providing a first nucleic acid sequence,
  providing a second nucleic acid sequence,
  providing a hybridization composition according to any of embodiments 1-31, and
  combining the first and the second nucleic acid sequence and the hybridization composition for at least a time period sufficient to hybridize the first and second nucleic acid sequences.

Embodiment 35

A method of hybridizing nucleic acid sequences comprising:
  providing a first nucleic acid sequence, and
  applying a hybridization composition according to any of embodiments 1-31 to said first nucleic acid sequence for at least a time period sufficient to hybridize the first and second nucleic acid sequences.

Embodiment 36

The method according to embodiments 30 or 31, wherein the polar aprotic solvent is defined according to any of embodiments 2-6 or 11-17.

Embodiment 37

The method according to any of embodiments 30-36, wherein a sufficient amount of energy to hybridize the first and second nucleic acids is provided.

Embodiment 38

The method according to embodiment 37, wherein the energy is provided by heating the hybridization composition and nucleic acid sequence.

Embodiment 39

The method according to embodiment 38, wherein the heating step is performed by the use of microwaves, hot baths, hot plates, heat wire, peltier element, induction heating or heat lamps.

Embodiment 40

The method according to any one of embodiments 32-39, wherein the first nucleic acid sequence is double stranded and the second nucleic acid is single stranded.

Embodiment 41

The method according to any one of embodiments 32-40, wherein the denaturation and hybridization steps occur separately.

Embodiment 42

The method according to any one of embodiments 32-41, wherein the step of hybridizing includes the steps of heating and cooling the hybridization composition and nucleic acid sequences.

Embodiment 43

The method according to any one of embodiments 32-42, wherein the step of hybridization takes less than 8 hours.

Embodiment 44

The method according to embodiment 43, wherein the step of hybridization takes less than 1 hour.

Embodiment 45

The method according to embodiment 44, wherein the step of hybridization takes less than 30 minutes.

Embodiment 46

The method according to embodiment 45, wherein the step of hybridization takes less than 15 minutes.

Embodiment 47

The method according to embodiment 46, wherein the step of hybridization takes less than 5 minutes.

Embodiment 48

The method according to any one of embodiments 32-47, wherein the cooling step takes less than 1 hour.

Embodiment 49

The method according to embodiment 48, wherein the cooling step takes less than 30 minutes.

Embodiment 50

The method according to embodiment 49, wherein the cooling step takes less than 15 minutes.

Embodiment 51

The method according to embodiment 50, wherein the cooling step takes less than 5 minutes.

Embodiment 52

The method according to any one of embodiments 32-51, wherein the first nucleic acid sequence is in a biological sample.

Embodiment 53

The method according to embodiment 52, wherein the biological sample is a cytology or histology sample.

Embodiment 54

The method according to any one of embodiments 32-53, wherein the hybridization composition comprises one phase at room temperature.

Embodiment 55

The method according to any one of embodiments 32-53, wherein the hybridization composition comprises multiple phases at room temperature.

Embodiment 56

The method according to embodiment 55, wherein the hybridization composition comprises two phases at room temperature.

Embodiment 57

The method according to embodiment 55 or 56, wherein the phases of the hybridization composition are mixed.

Embodiment 58

The method according to any one of embodiments 32-57, further comprising a blocking step.

Embodiment 59

Use of a hybridization composition comprising between 1 and 95% (v/v) of at least one polar aprotic solvent in hybridization assays.

Embodiment 60

Use of a composition according to embodiment 59, wherein the hybridization composition is according to any one of embodiments 1 to 31.

The invention claimed is:

1. A hybridization composition comprising a mixture of at least one nucleic acid sequence, at least one polar aprotic solvent in an amount effective to denature double-stranded nucleotide sequences, an accelerating agent, and at least one additional component selected from the group consisting of: buffering agents, salts, chelating agents, detergents, and blocking agents, wherein less than 10% of the hybridization composition is formamide, wherein the polar aprotic solvent is not dimethyl sulfoxide (DMSO) and has lactone, sulfone, sulfite, and/or carbonate functional groups and wherein the at least one nucleic acid sequence is a FISH or CISH probe;

wherein the at least one polar aprotic solvent comprises a polar aprotic solvent selected from the group consisting of:

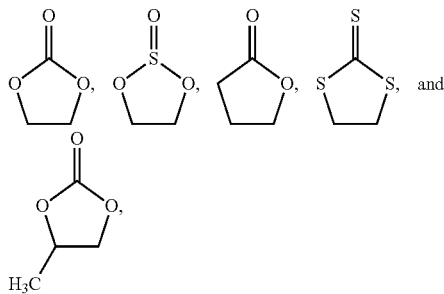

and
wherein the accelerating agent is selected from (i) a polymer, (ii) a protein, (iii) a glycol, (iv) glycerol, (v) combinations thereof, and (vi) organic solvents.

2. The hybridization composition according to claim 1, wherein the concentration of polar aprotic solvent is about 1% to 90% (v/v).

3. The hybridization composition according to claim 1 or 2, wherein the concentration of polar aprotic solvent is 5% to 10% (v/v).

4. The hybridization composition according to claim 1 or 2, wherein the concentration of polar aprotic solvent is 10% to 20% (v/v).

5. The hybridization composition according to claim 1 or 2, wherein the concentration of polar aprotic solvent is 20% to 30% (v/v).

6. The hybridization composition according to claim 1, wherein the polar aprotic solvent is non-toxic.

7. The hybridization composition according to claim 1, with the proviso that the composition does not contain formamide.

8. The hybridization composition according to claim 1, wherein the composition contains less than 2% formamide.

9. The hybridization composition according to claim 1 wherein the composition contains less than 1% formamide.

10. The hybridization composition according to claim 1, wherein the polar aprotic solvent has a dispersion solubility parameter between 17.7 to 22.0 MPa1/2, a polar solubility parameter between 13 to 23 MPa1/2, and a hydrogen bonding solubility parameter between 3 to 13 MPa1/2.

11. The hybridization composition according to claim 1, wherein the further at least one polar aprotic solvent is selected from the group consisting of: 2,3-butylene carbonate, γ-butyrolactone, caprolactone (epsilon), chloro maleic anhydride, chloroethylene carbonate, chloronitromethane, citraconic anhydride, crotonlactone, 5-cyano-2-thiouracil, dimethyl sulfate, dimethyl sulfone, diphenyl sulfone, ethanesulfonylchloride, ethylene carbonate, ethylene glycol sulfate, glycol sulfite, methyl alpha bromo tetronate, methyl phenyl sulfone, methyl sulfolane, methyl-4-toluenesulfonate, N-phenyl sydnone, phthalic anhydride, 1,3-propane sultone, β-propiolactone, propylene carbonate, saccharin, sulfanilamide, sulfolane, trimethylene sulfide-dioxide, and trimethylene sulfite.

12. The hybridization composition according to claim 1, wherein the salt is NaCl and/or the buffering agent is phosphate buffer.

13. The hybridization composition according to claim 12, wherein the composition further comprises dextran sulfate present at a concentration of 10% to 40%, and wherein the NaCl is present at a concentration of 0 mM to 1200 mM, and/or the phosphate buffer is present at a concentration of 0 mM to 50 mM.

14. The hybridization composition according to claim 13, wherein the dextran sulfate is present at a concentration of 10% to 30%, the NaCl is present at a concentration of 300 mM to 600 mM, and/or the phosphate buffer is present at a concentration of 5 mM to 20 mM.

15. The hybridization composition according to claim 1, wherein:
the accelerating agent is selected from the group consisting of: formamide, glycerol, propylene glycol, 1,2-propanediol, diethylene glycol, ethylene glycol, glycol, and 1,3 propanediol, and the buffering agent is citric acid buffer.

16. The hybridization composition according to claim 1, wherein:
the accelerating agent is selected from the group consisting of: formamide at a concentration of 0.1-5%, glycerol at a concentration of 0.1% to 10%, propylene glycol at a concentration of 0.1% to 10%, 1,2-propanediol at a concentration of 0.1% to 10%, diethylene glycol at a concentration of 0.1% to 10%, ethylene glycol at a concentration of 0.1% to 10%, glycol at a concentration of 0.1% to 10%, and 1,3 propanediol at a concentration of 0.1% to 10%, and
the buffer is citric acid buffer at a concentration of 1 mM to 50 mM.

17. The hybridization composition according to claim 1, wherein the blocking agent is selected from the group consisting of: total human DNA, herring sperm DNA, salmon sperm DNA, and calf thymus DNA.

18. The hybridization composition according to claim 17, wherein the total human DNA, herring sperm DNA, salmon sperm DNA, or calf thymus DNA is present at a concentration of 0.01 to 10 µg/µL.

19. The hybridization composition according to claim 1, comprising 40% of at least one polar aprotic solvent, 300 mM NaCl, and 5 mM phosphate buffer.

20. The hybridization composition according to claim 1, comprising 15% (v/v) of at least one polar aprotic solvent, 600 mM NaCl, 10 mM phosphate buffer, 0.1 µg/µL total human DNA and further comprising 20% dextran sulfate.

21. The hybridization composition according to claim 1, comprising:
at least one polar aprotic solvent at a concentration of 15% (v/v),
600 mM NaCl, 10 mM citric acid buffer pH 6.2,
0.1 µg/µL herring sperm DNA, salmon sperm DNA, or calf thymus DNA, or
0.5% formamide, 1% ethylene glycol, or 1% 1,3 propanediol and further comprising 20% dextran sulfate.

22. The hybridization composition according to claim 1, comprising more than one phase at room temperature.

23. The hybridization composition according to claim 22, comprising two phases at room temperature.

24. The hybridization composition according to claim 22, comprising three phases at room temperature.

25. The hybridization composition according to claim 1, wherein the at least one nucleic acid sequence is a FISH DNA probe.

26. The hybridization composition according to claim 1, wherein the at least one nucleic acid sequence comprises a detectable label.

27. The hybridization composition according to claim 1, further comprising up to 10% dextran sulfate.

28. The hybridization composition according to claim 1, further comprising up to 20% dextran sulfate.

29. The hybridization composition according to claim 1, further comprising an accelerating agent at a concentration from 1%-80%.

30. The hybridization composition according to claim 1, wherein the accelerating agent is dextran sulfate.

31. The hybridization composition according to claim 1, wherein the accelerating agent is selected from the group consisting of PVP, heparin, dextran sulfate, BSA, ethylene glycol, 1,3 propanediol, propylene glycol, diethylene glycol, glycerol, combinations thereof, formamide, dimethylformamide and DMSO.

* * * * *